United States Patent
Norén

(10) Patent No.: US 7,283,865 B2
(45) Date of Patent: Oct. 16, 2007

(54) DEVICE AND METHOD FOR DETERMINING A CARDIAC CONDITION USING A COMPLEX SIGNAL FORMED FROM A DETECTED CARDIAC SIGNAL

(75) Inventor: Kjell Norén, Solna (SE)

(73) Assignee: St. Jude Medical AB, Jarfalla (SE)

( * ) Notice: Subject to any disclaimer, the term of this patent is extended or adjusted under 35 U.S.C. 154(b) by 145 days.

(21) Appl. No.: 10/505,013

(22) PCT Filed: Feb. 27, 2003

(86) PCT No.: PCT/SE03/00338

§ 371 (c)(1),
(2), (4) Date: Aug. 18, 2004

(87) PCT Pub. No.: WO03/071945

PCT Pub. Date: Sep. 4, 2003

(65) Prior Publication Data

US 2005/0107836 A1 May 19, 2005

(30) Foreign Application Priority Data

Feb. 28, 2002 (SE) .................................. 0200624

(51) Int. Cl.
*A61B 5/02* (2006.01)
*A61B 5/04* (2006.01)
*A61N 1/00* (2006.01)
(52) U.S. Cl. ...................... 600/518; 600/481; 600/485; 600/509; 600/513; 600/515; 607/4; 607/5; 607/7; 607/9; 607/14
(58) Field of Classification Search ................ 600/481, 600/485, 509, 513, 515, 518; 128/920; 607/4, 607/5, 14, 27, 32, 2
See application file for complete search history.

(56) References Cited

U.S. PATENT DOCUMENTS

| 3,173,095 A | * | 3/1965 | Wagner | 327/362 |
| 5,003,976 A | * | 4/1991 | Alt | 607/18 |
| 5,020,540 A | * | 6/1991 | Chamoun | 600/515 |
| 5,092,341 A | * | 3/1992 | Kelen | 600/515 |

(Continued)

OTHER PUBLICATIONS

"A Method For Determining High-Resolution Activation Time Delays in Unipolar Cardiac Mapping," Shors et al, IEEE Trans. On Biomedical Engineering, vol. 43, No. 12, Dec. 1996, pp. 1192-1196.

(Continued)

*Primary Examiner*—Carl Layno
*Assistant Examiner*—Natasha Patel
(74) *Attorney, Agent, or Firm*—Schiff Hardin LLP

(57) ABSTRACT

In a device and a method for determining a cardiac condition from a detected cardiac signal, an input signal is formed from the detected cardiac signal and supplied to an analysis unit. The analysis unit forms an analysis signal from the input signal, having a real part substantially corresponding to the input signal and an imaginary part that is a predetermined transformation of the input signal. A calculation unit operates on the analysis signal to calculated at least two heart-related parameters therefrom. The heart-related parameters are supplied to a processing unit that combines the heart-related parameters in a predetermined manner for identifying a cardiac condition.

33 Claims, 19 Drawing Sheets

U.S. PATENT DOCUMENTS

| | | | |
|---|---|---|---|
| 5,437,285 A * | 8/1995 | Verrier et al. | 600/515 |
| 5,545,182 A * | 8/1996 | Stotts et al. | 607/5 |
| 5,578,061 A | 11/1996 | Stroetmann et al. | |
| 5,596,993 A | 1/1997 | Oriol et al. | |
| 5,755,671 A | 5/1998 | Albrecht et al. | |
| 5,891,178 A * | 4/1999 | Mann et al. | 607/27 |
| 5,944,669 A * | 8/1999 | Kaib | 600/512 |
| 5,954,666 A | 9/1999 | Snell | |
| 6,070,100 A | 5/2000 | Bakels et al. | |
| 6,735,466 B1 * | 5/2004 | Haghighi-Mood | 600/515 |

OTHER PUBLICATIONS

"A Method For Determining High-Resolution Activation Time Delays in Unipolar Cardiac Mapping," Shors, et al Computers in Cardiology 1994, pp. 157-159.

* cited by examiner

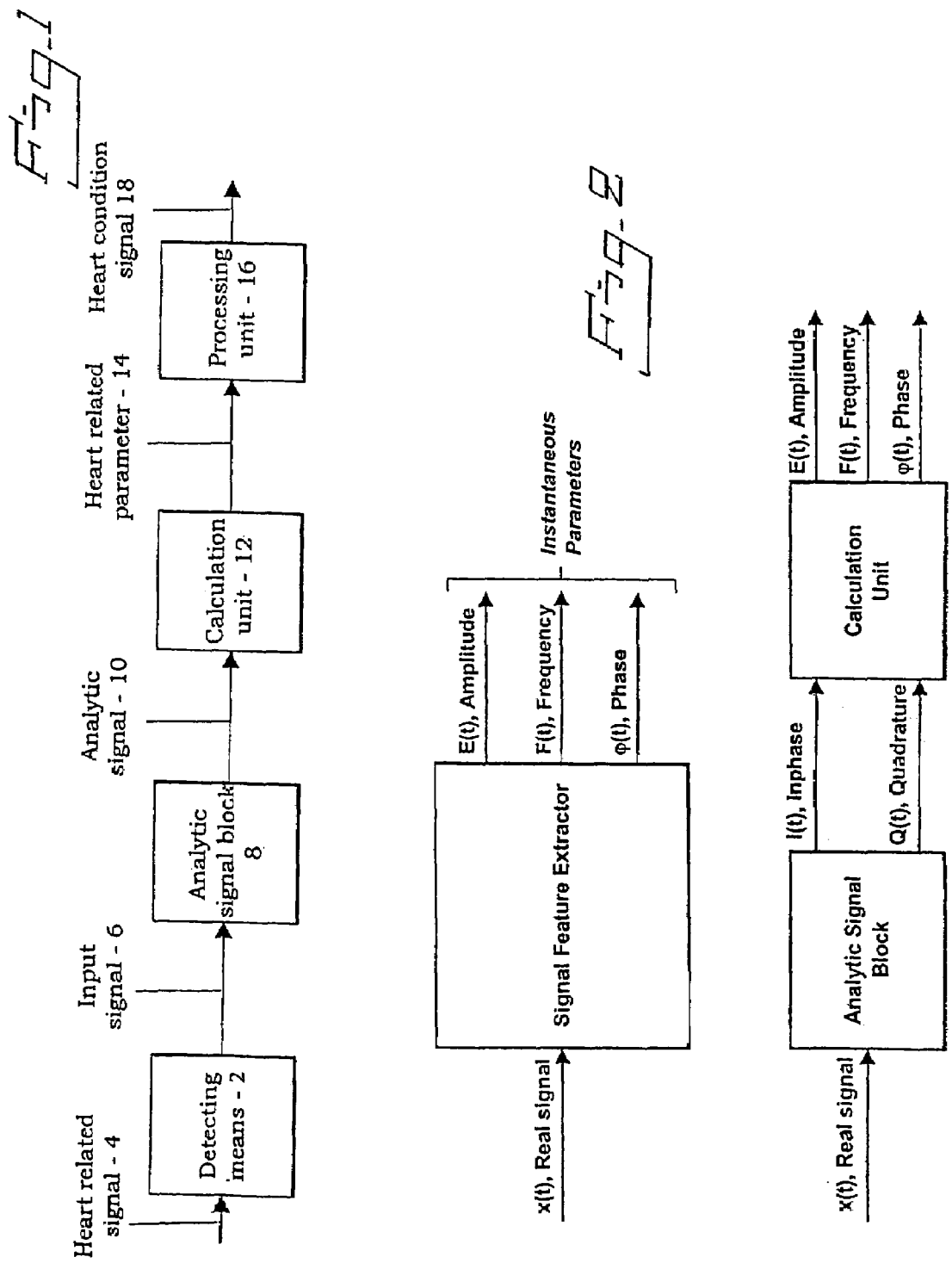

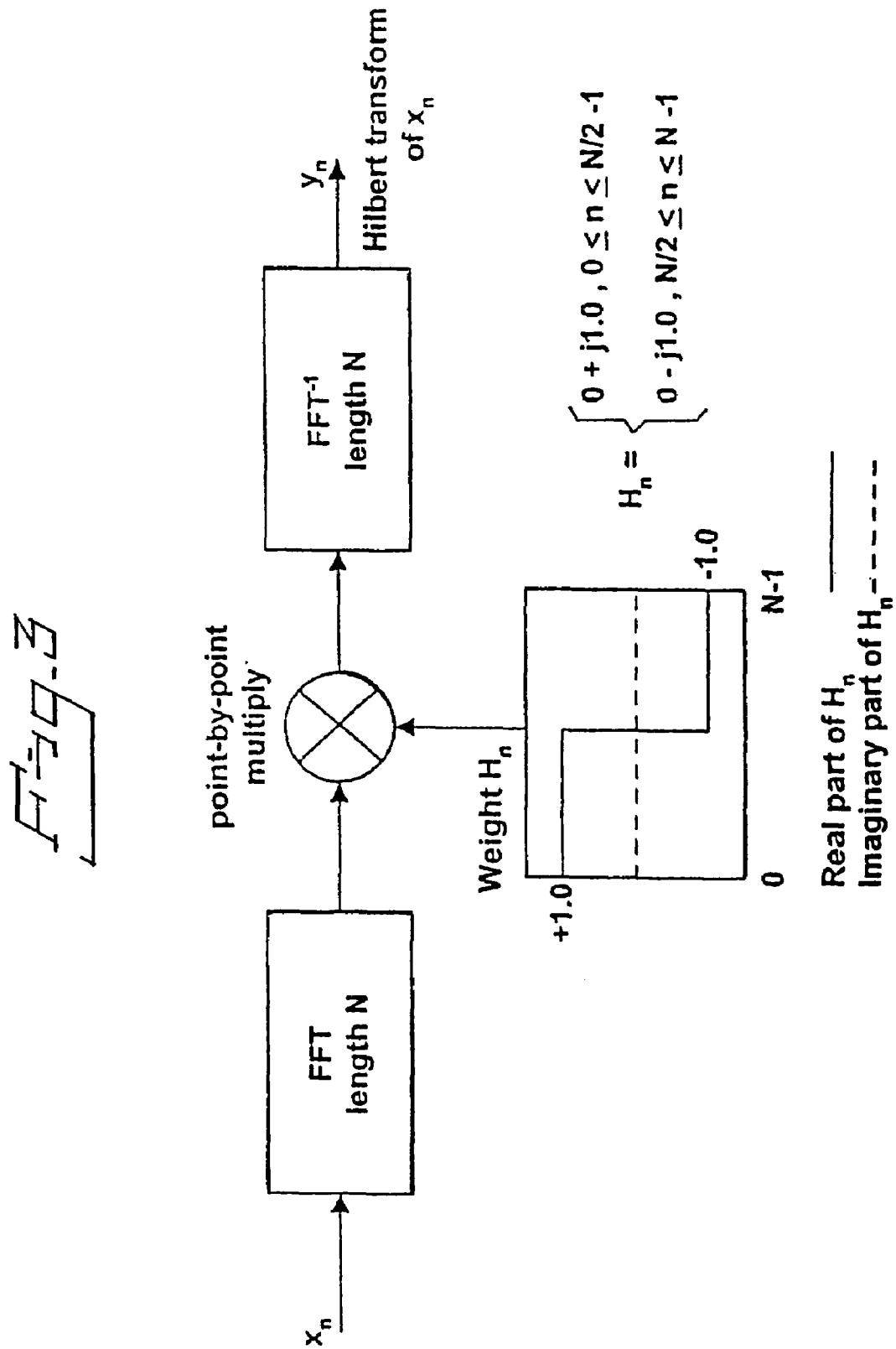

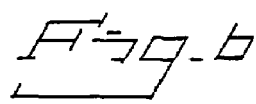
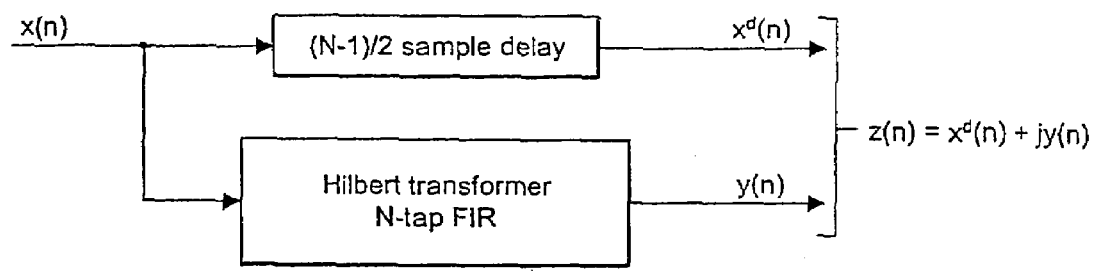

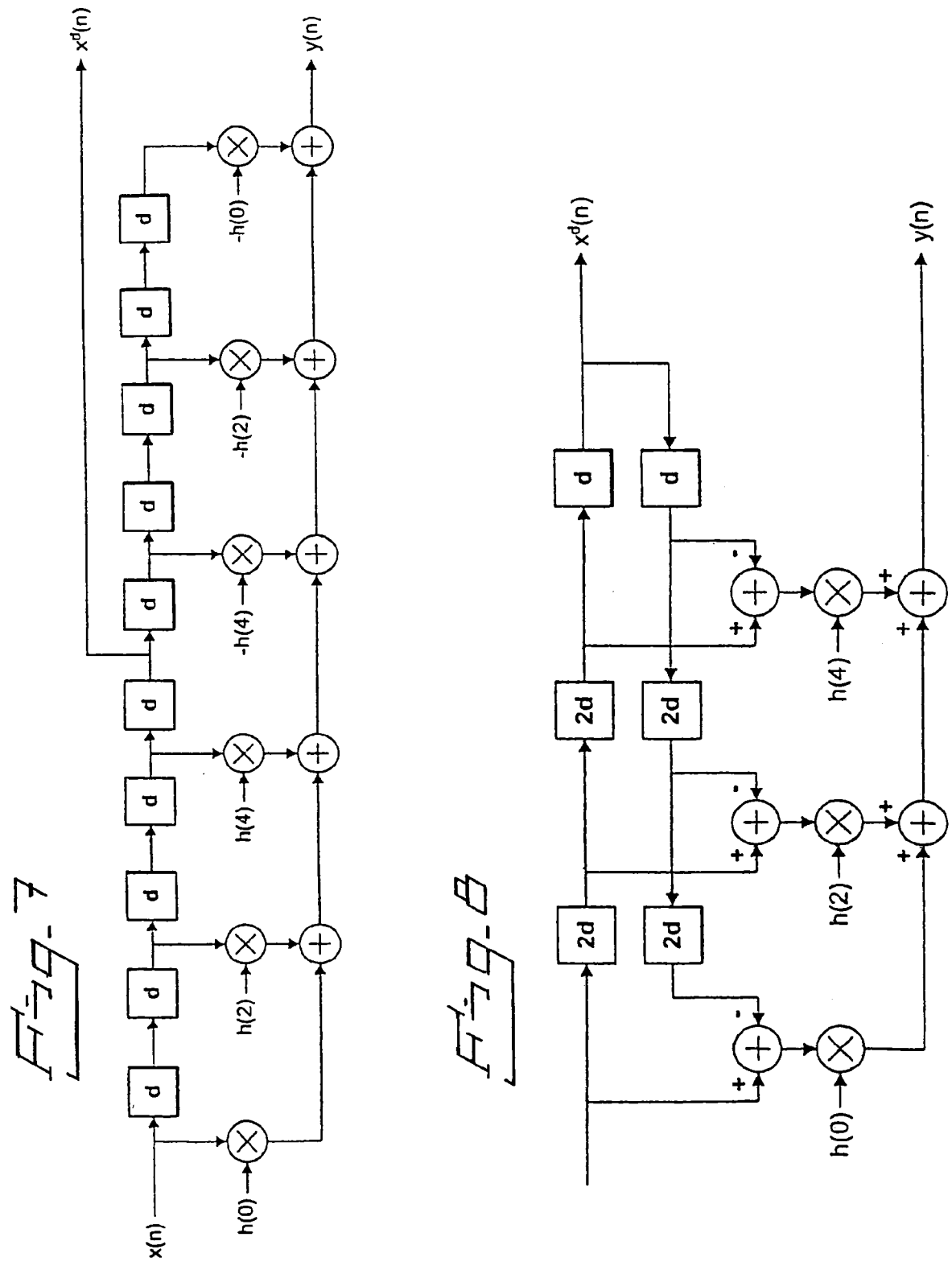

Fig. 12
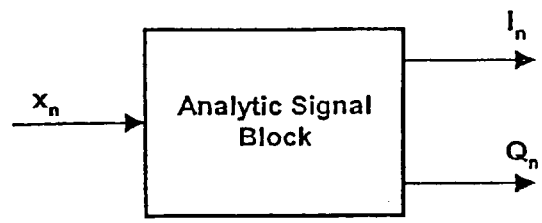
Calculation Unit
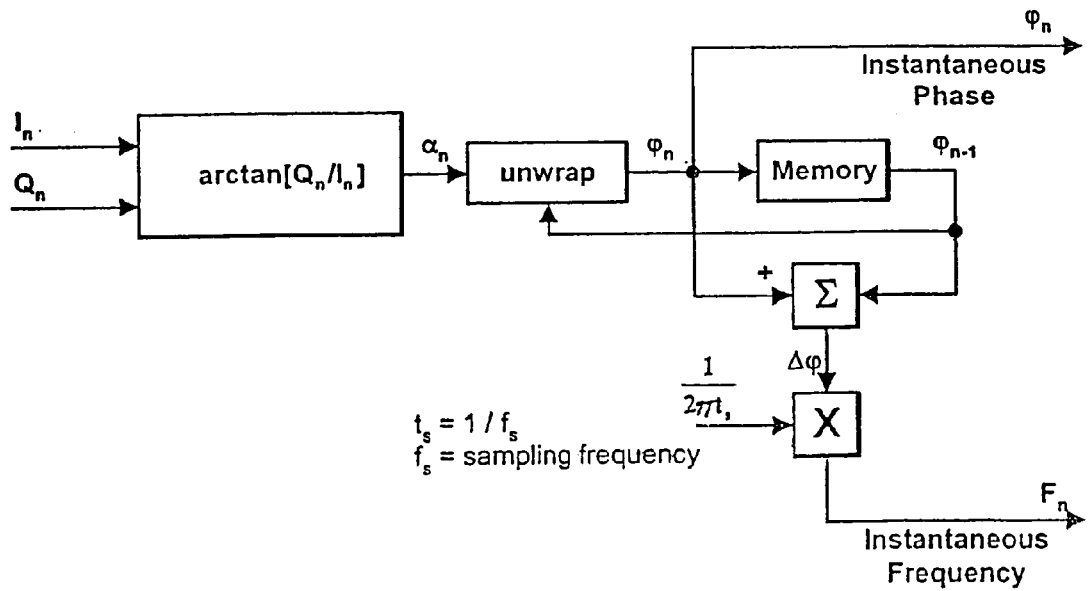
$t_s = 1/f_s$
$f_s$ = sampling frequency Fig. 13
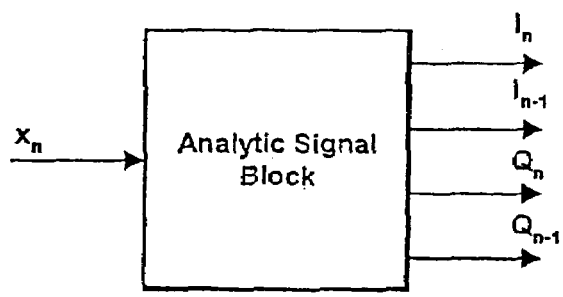
Calculation Unit
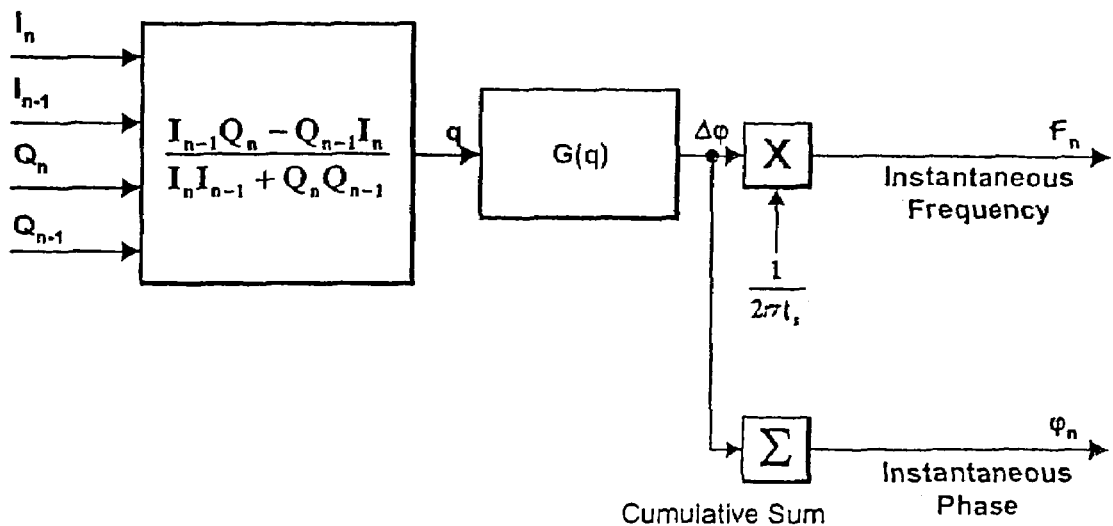

DEVICE AND METHOD FOR DETERMINING A CARDIAC CONDITION USING A COMPLEX SIGNAL FORMED FROM A DETECTED CARDIAC SIGNAL

BACKGROUND OF THE INVENTION

1. Field of the Invention

The present invention relates to a device and method for determining a cardiac condition of the type wherein a detected cardiac signal is supplied to a signal evaluation unit that undertakes mathematical operations on the detected signal, or a signal derived therefrom, to obtain parameters that are analyzed to identify a particular cardiac condition 2. Description of the Prior Art The status of the heart can be studied by measuring different parameters, e.g. the heart rate measured via intracardially obtained ECG (also denoted intracardiac electrogram, IEGM). By identifying certain properties in the beat-to-beat rate, measured via the electrode system, calculations may be executed in the implantable cardioverter-defibrillator (ICD) to determine whether ventricular fibrillation is present resulting in that a defibrillation shock should be delivered. Far field sensing and misinterpretation of supraventricular (emanating from the atrium) tachycardias may result in that inappropriate shocks are delivered. Therefore, a fast, sensitive and specific detection of ventricular fibrillation (VF) is of utmost importance for the patient.

It is generally difficult to distinguish between different types of tachycardia and fibrillation. In some patient also ventricular flutter may occur.

SUMMARY OF THE INVENTION

An object of the present invention is to provide a technique for processing sensor signals such as pressure, impedance and IEGM for fast and reliable detection (discrimination), classification of ventricular tachycardia, ventricular fibrillation and also atrial fibrillation.

The above object is achieved in accordance with the present invention in a device and method for determining a cardiac condition, wherein a cardiac (heart-related) signal is detected and the detected signal is supplied as an input signal to an analysis unit that produces an analysis signal based on the input signal, composed of a real part essentially corresponding to the input signal and an imaginary part formed as a predetermined transformation of the input signal. The analysis signal is then supplied to a calculation unit wherein at least two heart-related parameters are calculated from the analysis signal. The heart-related parameters are then supplied to a processing unit that combines the calculated heart-related parameters in a predetermined manner to identify a particular cardiac condition.

The extracted information representing the characteristic rate (instantaneous frequency) and amplitude (instantaneous amplitude) obtained from an analytical signal is used for the detection of severe hemo-dynamical conditions in the heart.

There are numerous patents and articles describing different algorithms used for processing of IEGM and other describe the use of impedance and pressure to obtain a good detection.

The use of a specific technique based upon the processing of a transformed complex signal for performing discrimination and detection of ventricular fibrillation, ventricular tachycardia and atrial fibrillation etc. is not known.

The inventive concept is based upon processing an analytical signal where the Hilbert Transform or an approximate Hilbert Transform is used to create the imaginary part of the complex signal, which is a new approach in the application area of discrimination and detection of different functional states of the heart.

An advantage of an implantable heart therapy device that includes the implantable heart condition determining device according to the present invention is that the therapy device is enable to rapidly and accurately detect a severe heart condition and then to initiate an adequate heart therapy. In the case the heart therapy device being an implantable defibrillator, that includes large capacitors that must be energy loaded prior it is possible to generate and apply a defibrillation shock, the loading of the capacitors can be initiated earlier because of the rapid detection of e.g. ventricular fibrillation of the heart.

Another advantage of the present invention is achieved if the heart therapy is an implantable heart stimulator. In that case an initiated therapy intended to break e.g. a ventricular tachycardia may be returned more rapidly to normal pacing therapy.

According to a still further embodiment of the present invention the heart therapy device also includes a confirmation unit that confirms a "new" heart condition that occurs after a specific therapy has been applied successfully to the heart.

DESCRIPTION OF THE DRAWINGS

FIG. 1 is a block diagram illustrating an implantable heart condition determining device according to the present invention.

FIG. 2 shows in a block schematic form the signal feature extractor according to the present invention.

FIG. 3 is a block diagram illustrating the analytic signal block according to a preferred embodiment of the present invention.

FIG. 6 shows a general structure of a discrete FIR Hilbert transformer.

FIG. 7 shows an 11-tap structure for a Type III FIR Hilbert transformer.

FIG. 8 illustrates an alternative architecture of a Type III FIR Hilbert transformer.

FIG. 12 shows a block diagram illustrating an example of a first method used by the calculation unit.

FIG. 13 shows a block diagram illustrating an example of a second method used by the calculation unit.

DESCRIPTION OF THE PREFERRED EMBODIMENTS

Figure 4:
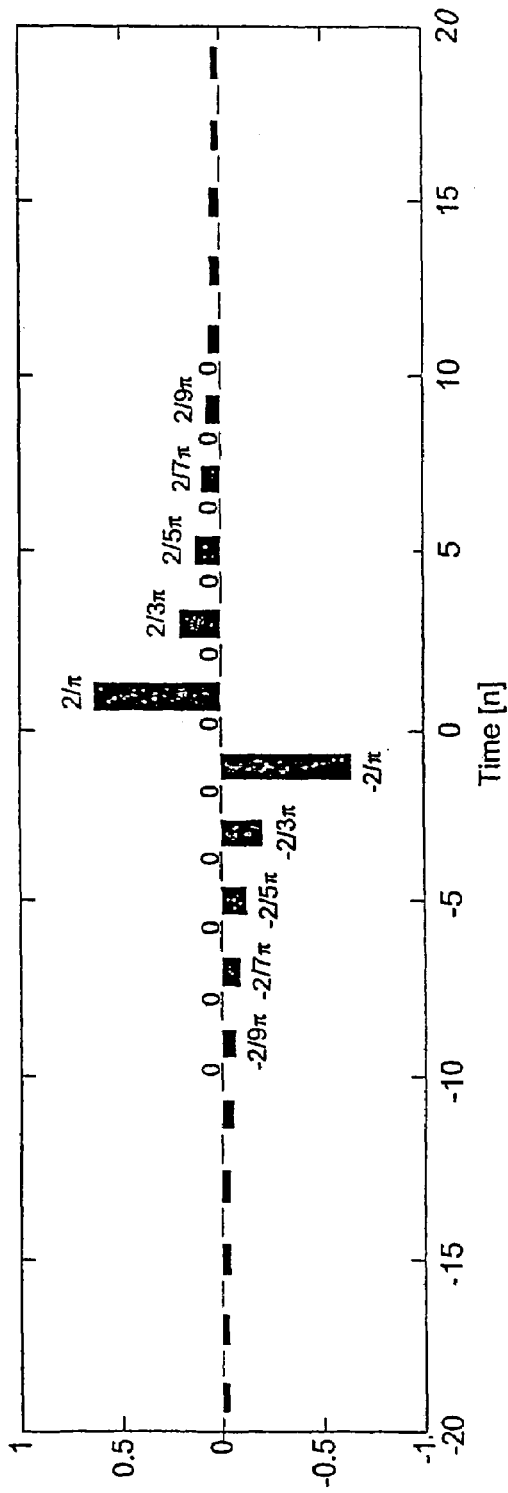
FIG. 4 shows a plot of the discrete impulse response for $f_s=1$.

FIG. 1 shows a block diagram illustrating an implantable heart condition determining device according to the present invention.

The implantable heart condition determining device includes a detector 2 arranged to detect a heart related signal 4 and to generate a corresponding input signal 6 in dependence of the heart related signal. The input signal is applied to an analytic signal circuit 8 that provides an analytic signal 10 based on the input signal, the analytic signal having a real part essentially being the input signal and an imaginary part being a predefined transformation of the input signal. The analytic signal is applied to a calculation unit 12 that calculates at least one heart related parameter 14 from the analytic signal and the heart related parameter(s) is then applied to a processing unit 16 in order to identify heart conditions and to generate a heart condition signal 18 in dependence thereto.

As discussed above one important feature of the present invention is to create an analytic signal based upon a detected signal obtained from a detected heart related parameter. The analytic signal is preferably created by using the Hilbert transform.

The concept of using the Hilbert transform in order to obtain an analytic signal is well known in communication theory and e.g. for non-linear analysis of mechanical vibration—especially seismic waves from earthquakes. The Hilbert transform has also been used in medical technology.

For example, U.S. Pat. No. 5,596,993 discloses a fetal data processing system and method for monitoring the condition of a fetus. A fetus heart rate time series is received and sampled and made analytic by e.g. a digital Hilbert Transformer. A non-linear time frequency transformation is then performed on the analytic heart rate signal. The obtained transformed signal may then be used to allow more accurate evaluations of overall fetal well-being including monitoring of changes in fetal state, fetal breathing movements, fetal body movements, fetal heart rate accelerations and decelerations etc. In this known device a further transformation is made of the analytic signal before evaluation is performed.

A similar use of the Hilbert transform is known from Shors, S. M. et al. "A method for determining high-resolution activation time delays in unipolar cardiac mapping", IEEE Transactions on Biomedical Engineering. IEEE, USA, December 1996, Vol. 43, pp. 1192-1196, ISSN 0018-9294.

In this article the Hilbert transform is applied on a cross correlation between two filtered, differentiated electrograms in order to locate a zero crossing of the electrogram.

In U.S. Pat. No. 5,437,285 a method is known for predicting susceptibility to sudden cardiac death simultaneously assessing cardiac electrical stability, by analyzing e.g. a beat-to-beat alternation in a T-wave of an ECG of a patients heart, and automatic influence, by analyzing e.g. a magnitude of heart rate variability in the ECG. The analysis of the T-wave alternans involves using an analytical process, e.g. a complex demodulation.

However, in the specific medical field of implantable heart devices no use of the Hilbert transform is known to obtain an analytic signal of a detected signal in order to be able to perform fast and accurate detection of heart conditions.

The following describes how an analytic signal is obtained according to a first embodiment of the present invention.

In order to increase the understanding of the present invention an introduction is given where the analytic signal and the Hilbert transform are described.

Introduction

A real signal x(t) contains equal amounts of positive and negative frequencies if we perform a spectral analysis. We always have $|x(-f)|=|x(f)|$ where x(f) denotes the spectrum of the real signal x(t). The reason for this is the Euler identity $$e^{j\theta}=\cos(\theta)+j\sin(\theta)$$

Of which follows that $$\cos(\theta) = \frac{e^{j\theta} + e^{-j\theta}}{2}$$

$$\sin(\theta) = \frac{e^{j\theta} - e^{-j\theta}}{2j}$$

By setting $\theta=\omega t+\alpha$ we see that both sine and cosine (and hence all real sinusoids) consist of a sum of equal and opposite circular motion.

A complex sinusoid is simpler than a real sinusoid because the complex sinusoid consists of one frequency while the real consists of two frequencies, one positive and one negative.

$$Ae^{j(\omega t+\alpha)} \text{ Complex}$$

$$A\sin(\omega t+\alpha) \text{ Real}$$

The real sinusoid is "twice as complicated" than the complex sinusoid. Another property of the complex sinusoid is that the modulus is constant. To find the amplitude of the complex sinusoid, just take the square root of the real and imaginary parts. To find the instantaneous frequency of a signal just perform differentiation of the phase.

A signal, which has no negative-frequency components, is called an analytic signal.

Any real sinusoid can be converted to a positive-frequency complex sinusoid by generating a phase-quadrature component to serve as the "imaginary part".

For instance:

$$A\cos(\omega t+\alpha) \rightarrow Ae^{j(\omega t+\alpha)}=A\cos(\omega t+\alpha)+jA\sin(\omega t+\alpha)$$

For the more general case when the signal x(t) is expressed as a sum of many sinusoids, a filter can be constructed which shifts each sinusoidal component by a quarter cycle. This is called a Hilbert transform filter. If H{x(t)} denotes the output from the Hilbert-transform filter then the (complex) analytic signal is $$z(t)=X(t)+jH\{X(t)\} \quad (*)$$

A representation of a magnitude spectrum of the analytical signal z(t) has only positive frequency components.

The Analytic Signal Concept

The concept of the Analytic Signal was introduced by Gabor D. (1946): "Theory of communication". J. IEE London 93, pp. 429-457 in 1946 by proposing a consistent way to define the instantaneous phase and amplitude for an arbitrary signal x(t). This is done by the construction of an analytic signal z(t) which is a complex function of time defined by that the complex component is the Hilbert transform of the real signal; i.e. $z(t)=X(t)+jH\{X(t)\}$ Let the analytical signal be:

$$z(t)=X(t)+jy(t) \quad (1)$$

where x(t) is the original signal, j is the imaginary unit $j^2=-1$ and y(t) is the Hilbert transform of x(t) given by $$y(t) = \frac{1}{\pi}\int_{-\infty}^{+\infty} \frac{\chi(s)}{t-s} ds \quad (2)$$

The integral is calculated as the Cauchy principal value integral.

Thus the integration is performed as $$PV\frac{1}{\pi}\int_{-\infty}^{+\infty}\frac{\chi(s)}{t-s}ds \equiv \lim_{R\to\infty}\frac{1}{\pi}\int_{-R}^{+R}\frac{\chi(s)}{t-s}ds \quad (3)$$

It follows from (2) that the integral also can be identified as the convolution $$y(t)=(1/\pi t)\otimes X(t) \quad (4)$$

The Hilbert transform performs a 90-degree phase shift of all frequencies in the signal.

For this reason the notations I (In-phase signal) for x(t) and Q (Quadrature signal) for y(t) are often used in the literature.

Rewritten in polar form $$z(t)=E(t)e^{j\phi(t)} \quad (5)$$

where the instantaneous amplitude (envelope) (6) and instantaneous phase (7) are:

$$E(t)=|z(t)|=\sqrt{X^2(t)+y^2(t)} \quad (6)$$

$$\phi(t)=\arg\{z(t)\}=\arctan[y(t)/X(t)] \quad (7)$$

The envelope E(t) is sometimes called the local energy of the signal.

The time derivative of the phase angle $$\frac{d\varphi}{dt} = \frac{d}{dt}\arctan[y(t)/\chi(t)] \quad (8)$$

defines the characteristic frequency or instantaneous frequency by $$F(t) = \frac{1}{2\pi}\frac{d\varphi}{dt} \quad (9)$$

It follows from (8) by performing the operation that the time derivative of the phase angle can also be expressed as $$\varphi'(t) = \frac{x(t)y'(t) - y(t)x'(t)}{(x(t))^2 + (y(t))^2} \quad (10)$$
$$= \frac{x(t)y'(t) - y(t)x'(t)}{(E(t))^2}$$
$$= \text{Im}\left[\frac{Z'(t)}{Z(t)}\right]$$

where (') denotes the time derivative of the respective functions.

The time-derivative of the amplitude can be expressed as $$E'(t) = \frac{x(t)x'(t) - y(t)y'(t)}{E(t)} = E(t)\text{Re}\left[\frac{Z'(t)}{Z(t)}\right] \quad (11)$$

Below are some general properties of the Hilbert Transform:

The Hilbert transform of a constant is zero.
The Hilbert transform of a Hilbert transform is the negative of the original function.
A function and its Hilbert transform are orthogonal over the infinite interval.
The Hilbert transform of a real function is a real function.
The Hilbert transform of an even function is an odd function and the Hilbert transform of an odd function is an even function.
The Hilbert transform of the convolution of the two functions is the convolution of one with the Hilbert transform of the other.
A simple way to describe the Hilbert Transform of a time signal is that all frequency component is shifted −90° or a quarter of a wavelength in the time domain.

FIG. 2 shows in a block schematic form the signal feature extractor (at the top of FIG. 2) according to the present invention where the calculations of the characteristic amplitude, frequency and phase of a real signal are performed. The signal feature extractor is further separated into an analytic signal block and a calculation unit (at the bottom of FIG. 2).

The processed data can either be performed by using buffered or unbuffered samples. In the buffered case the measured samples are stored in a data buffer before the processing. This is typical if the analytical signal is calculated by FFT. The unbuffered case is typical when the analytical signal is determined by filtering (which of course also can be done using buffered data).

FIG. 2 does not show preprocessing such as bandpass filtering of the signal x(t) to cut out a frequency range of interest. Neither is any post-processing of the calculated parameters shown. A typical post-processing is to apply low-pass filtering on the output signals.

The analytic signal block and the calculation unit will be described in detail below.

Analytic Signal Block

The Hilbert transform and hence the analytic signal for a sampled real signal x(t) may generally be calculated in two ways. In the frequency domain by FFT approaches or in the time domain by the use of a Hilbert filter. These two ways will be described in the following.

Frequency Domain Hilbert Transform by FFT Approaches

The Hilbert transform and the Analytical signal are generated simultaneously.

1. Collect N samples of the signal x(t)
2. Perform an N-point FFT of the N-length sampled signal x(t)
3. Zero out the FFT-bins for negative frequencies, leaving a one-sided spectrum
4. Double the magnitude for positive frequencies
5. Perform an N-point inverse FFT, this gives z(t)=x(t)+jy(t)
6. Ready The Analytic signal z(t) is a complex signal (in the time domain). All of the previous discussions regarding the calculations of Instantaneous Phase, Instantaneous Frequency, and Instantaneous Amplitude applies.

FIG. 3 is a block diagram illustrating a preferred embodiment of the analytic signal block using FFT. The result of the inverse FFT is the Hilbert transform y(t). We already know x(t).

Time Domain Hilbert Transform (HT) by Using a Hilbert Filter

The Hilbert transform can be expressed by the convolution $$H\{x(t)\} = (1/\pi t) \otimes x(t)$$

which also can be rewritten as $$y(t) = h(t) \otimes x(t)$$

where h(t) is the impulse response of the HT.

In frequency plane:

$$Y(\omega) = H(\omega)^* X(\omega), \omega = 2\pi \int 10$$

$$H(\omega) = \begin{cases} -j, & \omega > 0 \\ +j, & \omega < 0 \end{cases}$$

The last equations are an illustration of that the HT can be interpreted as a filter.

The general inverse Fourier transform of an arbitrary frequency function $g(\omega)$ is $$f(t) = \frac{1}{2\pi} \int_{-\infty}^{+\infty} g(\omega) e^{j\omega t} d\omega$$

The following applies naturally directly $$g(\omega) = H(\omega) \Rightarrow h(t) = \frac{1}{\pi t}$$

In order to determine the Hilbert transform impulse response expression for a bandwidth-limited signal is the integration instead performed over the interval $\omega_s/2$ to $+-\omega_s/2$ where $\omega_s$ is the sampling frequency. (We also know that the discrete frequency response is periodic with a repetition interval $\omega_s$.)

$$h(t) = \frac{1}{2\pi} \int_{-\omega_s/2}^{+\omega_s/2} H(\omega) e^{j\omega t} dw$$

$$= \frac{1}{2\pi} \int_{-w_s/2}^{0} j e^{j\omega t} dw + \frac{1}{2\pi} \int_{0}^{+\omega_s/2} -j e dw + \frac{1}{2\pi} \int_{0}^{+\omega_s/2} -j e^{j\omega t} dw \Rightarrow$$

$$h(t) = \frac{1 - \cos(\omega_s t/2)}{\pi t}, h(0) = 0$$

To find the discrete version of h(t) is the continuous time variable t substituted with a discrete variable $nt_s$ where $t_s$ is the time between samples and n is a time domain index ( . . . , -2, -1, 0, 1, 2, . . . ). The time step between samples is $t_s = 1/f_s$, where $f_s$ is the sampling frequency.

$$h(nt_s) = \frac{1 - \cos(w_s n t_s / 2)}{n \pi t_s}$$

$$\omega_s = 2\pi f_s, t_s = 1/f_s \Rightarrow$$

$$h(nt_s) = \begin{cases} \frac{f_s(1 - \cos(n\pi))}{n\pi}, & n \neq 0 \\ 0, & n = 0 \end{cases}$$

For a normalized sampling frequency of one unit the last expression can be rewritten to $$h(n) = \frac{2\sin^2(n\pi/2)}{n\pi}$$

This is the formula usually found in the literature.

A plot of the discrete impulse response for $f_s=1$ is shown in FIG. 4. The h(n) series is anti-symmetric with all of the even coefficients equal to zero. The odd coefficients decrease by the factors 1/1, 1/3, 1/5, 1/7, 1/9, etc. This equals the Fourier series of a square wave. The illustrated series decays very slowly and is of infinite length. An ideal Hilbert transformer has this anti-symmetry property and amplitude of one unit across the entire frequency range.

In order to design a discrete Hilbert transformer there is need to truncate the series. The resulting implementation uses a discrete finite impulse response (FIR) filter structure that approximates the Hilbert transform. The signal processing is performed in the time domain.

Figure 5:
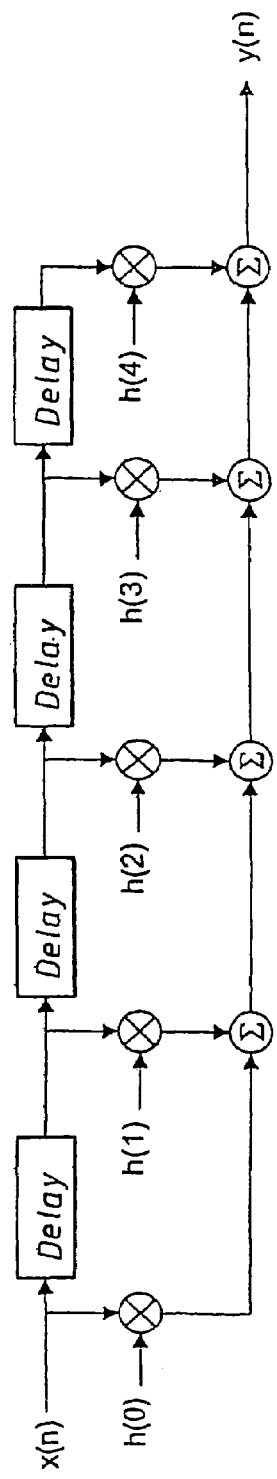
FIG. 5 illustrates an example of a general odd length FIR-filter structure.

An example of a general odd length FIR-filter structure is shown in FIG. 5. The number of taps is in this case and also the current input sample x(n) is weighted to the output y(n). The filter order number is 4 and is defined by the following expression.

$$y(n) = \sum_{k=0}^{4} h(k) x(n-k)$$

There are two digital FIR filter types available having anti-symmetric (or odd-symmetric) coefficients, type III or type IV, linear phase.

Type III has an odd number of taps (filter order number even) and type IV an even number of taps (filter order number odd). It is preferable to use type III for implementation as this has every second coefficient zero as listed above for the impulse response of the Hilbert transform. Type III is the only type where the phase distortion is easily removed. In order to make the filter causal a delay of N/2 term is included (where N+1 is the number of taps) which manifests itself as a linear phase when the analytical signal is generated. (Group delay G of an N+1 tap FIR filter is N/2 samples.)

The coefficients for a type IV filter are non-zero and the phase delay is more difficult to implement as the quotient N/2 is a non-integer number.

A general structure of a discrete FIR Hilbert transformer is shown in FIG. 6. The Hilbert transformer is of Type III and the number of taps N is odd. The group delay is (N−1)/2 samples and the analytical signal z(t) is constituted by the transformed signal y(t) and the delayed input signal $x^d(n)$. If for instance the number of taps is 15 then the delay is 7 samples.

For a Type III FIR Hilbert transformer is it easy to obtain the delayed input signal at the center tap of the FIR-filter. The example illustrated in FIG. 7 shows an 11-tap structure.

FIG. 8 illustrates an alternative architecture of a Type III FIR Hilbert transformer that exploits the alternate zero values and negative symmetry of the coefficients where the number of multiplications is decreased by a factor of two.

Other FIR Structures

The above FIR-structures involved a delay for the input signal and a filter chain to obtain the approximation of the Hilbert transform. The frequency roll-off is not symmetrical in the two paths and further is it only easy to tap off the delayed input signal by using the Type III structure. It is possible to avoid these problems by using a time-domain mixing technique that also allows a more general choice of filters. The aim of the processing is to create an I-channel for in-phase and a Q-channel for quadrature phase. From the point of view of the analytical signal is the essential part that the phase responses differ by 90°. The method described here can achieve almost identical responses of the I and Q channel magnitudes.

Figure 9:
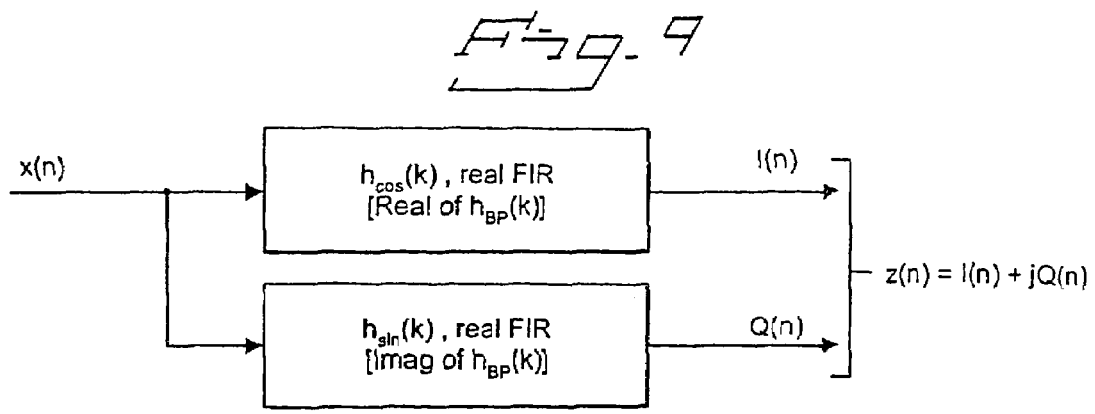
FIG. 9 illustrates an alternative mixed FIR filter structure.

Two separate FIR-filters are created that have essentially equal magnitude response. A standard k-tap low pass FIR filter is designed by using standard filter software. The bandwidth should be somewhat wider than the original real bandpass signal of interest. The resulting real coefficients of the lowpass filter are the multiplied by a complex exponential. This results in complex coefficients for a complex bandpass filter. The real part of the coefficients is used as coefficients for the in-phase FIR channel and the imaginary part for the quadrature channel. FIG. 9 illustrates this alternative mixed FIR filter structure.

Description of Expressions in the Algorithm:

$h_{LP}(k)$ real coefficients of the lowpass filter $e^{j\omega_c nt_s}$ the complex exponential where $\omega_c$ center frequency of original bandpass signal ($\omega_c=2\pi f_c$)

n the time index of LP-filter coefficients 0, 1, 2, ... k−1

$t_s$ sample time step, $t_s=1/f_s$ $f_s$ sample frequency of original bandpass signal sequence.

This gives the complex coefficients $h_{BP}(k)=h_{cos}(k)+jh_{sin}(k)$ which describes a complex bandpass filter centered around $f_c$ Hz. The real and imaginary parts are then used in two separate real-valued FIR filters.

The properties of the mixed filter illustrated in FIG. 9 are described below:

The $h_{LP}(k)$ coefficients could be doubled before the mixing. This avoids a loss of a factor two in the frequency magnitude responses of the two real FIR filters, which is a result of the mixing.

The $h_{LP}(k)$ coefficients could be windowed before mixing to reduce the passband ripple.

Odd and even-tap filters can be used.

If the original bandpass signal's, and the complex passband filter's, center frequency is $f_s/4$, then half of the coefficients of each real filter will be zero. The mixing Hilbert scheme have almost identical magnitude responses in the I and Q channels.

An alternative method to the above time domain complex FIR filter design is to perform the design in frequency domain as follows:

1. Determine the real $h_r(k)$ coefficients for a standard FIR bandpass filter centered around $\omega_c$.

2. Take FFT of the $h_r(k)$ coefficients which gives a "two-sided" $H_r(\omega)$ response.

3. To obtain $H_{BP}(\omega)$ set the negative frequency values of $H_r(\omega)$ to zero.

4. To obtain the complex coefficients $h_{BP}(k)$ take inverse FFT of $H_{BP}(\omega)$.

This will give the complex coefficients $h_{BP}(k)=h_{cos}(k)+jh_{sin}(k)$ for a complex bandpass filter centered around $f_c$.

Using IIR-Filter Structures

Discrete time Hilbert Transformers are usually designed as FIR-filters (linear phase). An alternative is to implement the Hilbert Transformer by an IIR-filter approach using a class of elliptic halfband IIR filters. Two such filters will form the analytical signal. The phase response will not be linear for the In-phase and Quadrature channel but the phase difference will be approximately 90° over a portion of the frequency axis. The main advantage is that a high order filter can be implemented with much less filter coefficients (multiplications) than for a FIR-structure. The IIR structure makes the computations far more efficient. A further simplification can be achieved by implementing the IIR-filters with no multipliers. The multipliers are substituted by shift-and-add operations.

An Infinite Impulse Response (IIR) digital filter design means that the output is a combination of previous output samples as well as the current and previous input samples.

The general IIR-filter output y(n) with the input x(n) can be described by function $$Y(z) = H(z)X(z) = \frac{b(0)+b(1)z^{-1}+\ldots+b(m)z^{-m}}{1+a(1)z^{-1}+\ldots a(p)z^{-p}} X(z)$$

The filter's transfer function H(z) is the Z-Transform of the system's impulse response.

The meaning of Z here is the unit-delay operator $z^{-1}$ and the constants a(i) and b(i) are the filter coefficients.

Figure 10:
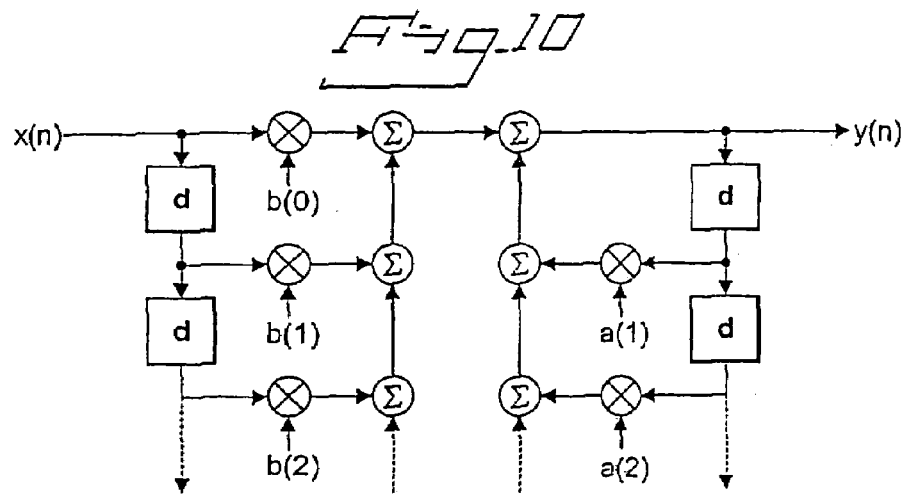
FIG. 10 shows a direct implementation of an IIR-filter.

A direct implementation of an IIR-filter is shown in FIG. 10 and is drawn directly from the filter equation and is called Direct Form 1.

High order filters are usually implemented by cascade coupling of second order filter sections in order to minimize the effects of coefficient truncation. (Even parallel realizations are possible.)

The numerator and denominator polynomials of the transfer function H(z) are factored into second order terms. The filter is then implemented as the cascade of the second order sections.

A second order section has the transfer function of the form $$H(z) = \frac{B0 + B1z^{-1} + B2z^{-2}}{1 + A1z^{-1} + A2z^{-2}}$$

Figure 11:
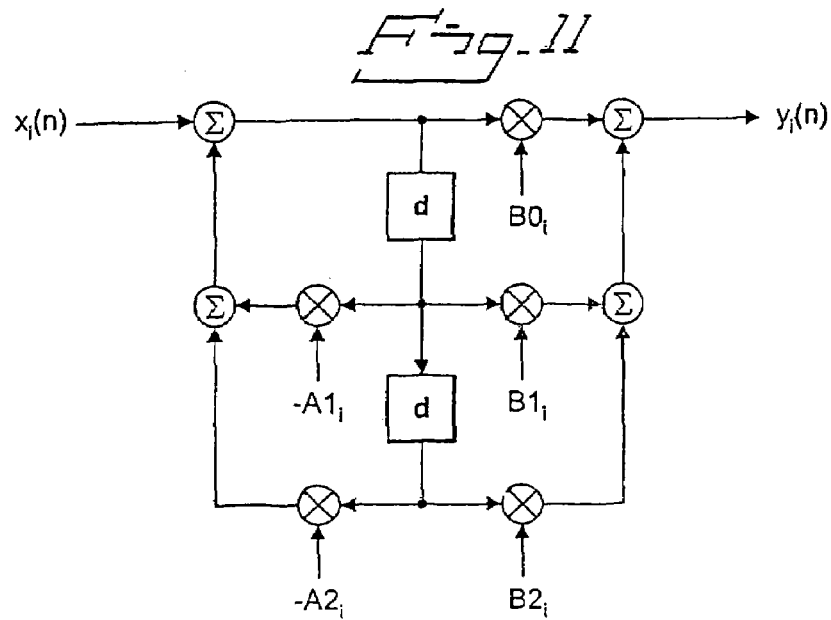
FIG. 11 shows another implementation of an IIR-filter, a so-called 1-D form.

The second order function can be implemented in a number of ways and in FIG. 11 one implementation is shown, a so-called 1-D form, for section number i.

A Continuous Solution

The methods described above are based on digital processing of discrete sampled values.

For completeness some words about an analog solution should be added. The analytical signal is a signal where the phase difference between the two components is 90 degrees. This may be achieved by the use of two parallel analog filters. The phase and amplitude can also be calculated using analog circuits.

Calculation Unit

The calculation unit will now be described in detail.

Two methods to find the frequency-related parameters, the frequency and phase, are available.

The first method is based on calculation of the phase and uses this for calculation of the frequency. Thus, there is a demand to unwrap the phase to avoid the wrapping around 360°.

The second method is based on calculation of the phase difference using different methods on consecutive samples of the analytical signal.

FIG. 12 shows a block diagram illustrating an example of the first method. Above in FIG. 12 the analytic signal block is shown where a real signal $x_n$ is made analytic and thus generates in-phase signal $I_n$ quadrature signal $Q_n$. These signals are then applied to calculation blocks (in the lower part of FIG. 12) in the calculation unit where $E_n$, $F_n$ and $\phi_n$ are calculated.

The phase angle of the analytical signal is calculated and unwrapped. The unwrapping process needs a memory.

FIG. 13 shows a block diagram illustrating an example of the second method. In FIGS. 12 and 13 the following signals are shown:

x—real signal.
I—in-phase signal.
Q—quadrature signal.
Index n—current sample.
Index n−1—previous sample.

At the top of FIG. 13 the analytic signal block is shown where a real signal $x_n$ is made analytic and thus generates in-phase signals $I_n$, $I_{n-1}$, and quadrature signals $Q_n$, $Q_{n-1}$. These signals are then applied to calculation blocks (in the lower part of FIG. 13) in the calculation unit where $E_n$, $F_n$ and $\phi_n$ are calculated.

The phase difference of the analytical signal is calculated using consecutive samples. In the function block G(q) the phase difference $\Delta\phi$ is calculated as arctan(q).

Different approximations to the arctan-function can be applied depending of the needed accuracy in the result.

The notation in FIG. 13 uses the terminology "current sample" and "previous sample" for the two consecutive samples. This can be changed to "next sample" and "current sample" and the indexing from n→n+1, n−1→n for the phase calculation in the figure.

Processing Unit

The instantaneous parameters, amplitude E, frequency F and phase $\phi$, determined by the calculation unit are applied to a processing unit for processing in order to identify heart related condition(s).

Generally, the determined heart related parameters (the amplitude, the frequency and the phase) may be combined in any predetermined way in the processing unit in order to identify a heart related condition. How the parameters are combined depends naturally of which heart related condition is to be identified. If, for example, a heart related condition is recognized by having high amplitude and a high frequency, the heart related parameters amplitude and frequency preferably are multiplied with each other.

According to a first preferred embodiment of the present invention, detection of ventricular fibrillation (VF) is performed by using right ventricular pressure (RVP) as the measured real signal being the input signal. Taken in consideration that the frequency in the measured RVP can be low even during VF and that the amplitude also is at a low level it was found that it would be feasible to mix the information from the frequency and amplitude of the RVP. It has been found that it is very advantageous to determine the quotient Q between the instantaneous frequency F and the instantaneous amplitude E that is determined by the calculation unit in the signal feature extractor. A normalized value of the quotient Q was used, $Q_{detect}=Q/Q_n$, where $Q_n$ is a 10 seconds average of Q during normal conditions, for instance during VVI 100 stimulation. A detection threshold at 400% of the normalized value was then set.

Figure 14:
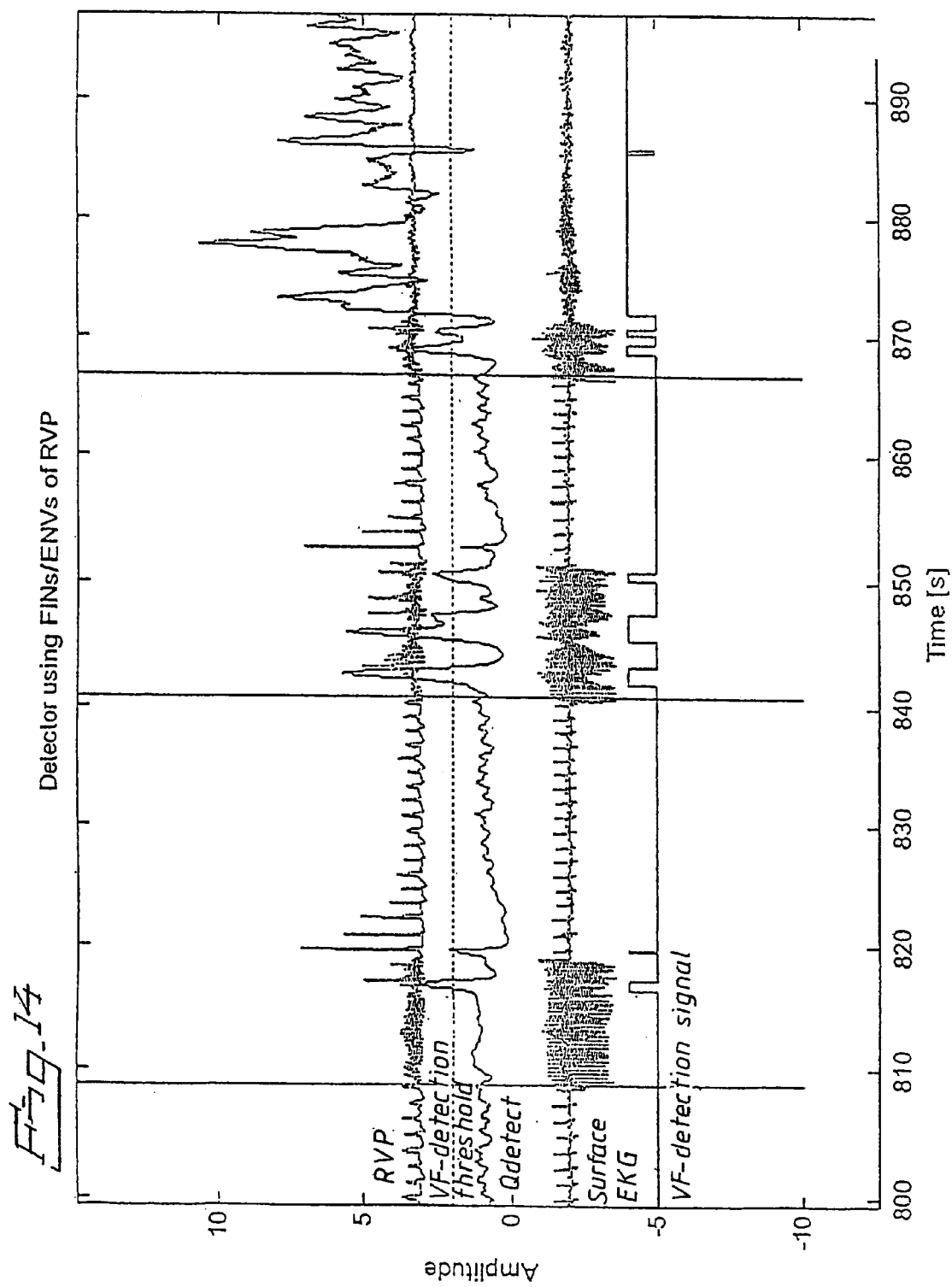
FIG. 14 is a legend of a ventricular tachycardia (VT) session followed by a ventricular fibrillation (VF) session illustrating a preferred embodiment of the present invention.

FIG. 14 is a legend of a ventricular tachycardia (VT) session followed by a ventricular fibrillation (VF) session and shows from above the RVP, a VF detection threshold, $Q_{detect}$, surface ECG and the logical VF-detection signal. The Y-axis represents the amplitude of $Q_{detect}$ and the x-axis the time in seconds.

When $Q_{detect}$ is greater than the VF detection threshold the logical VF-detection signal goes from its lower state to its higher VF-detecting state.

Figure 15:
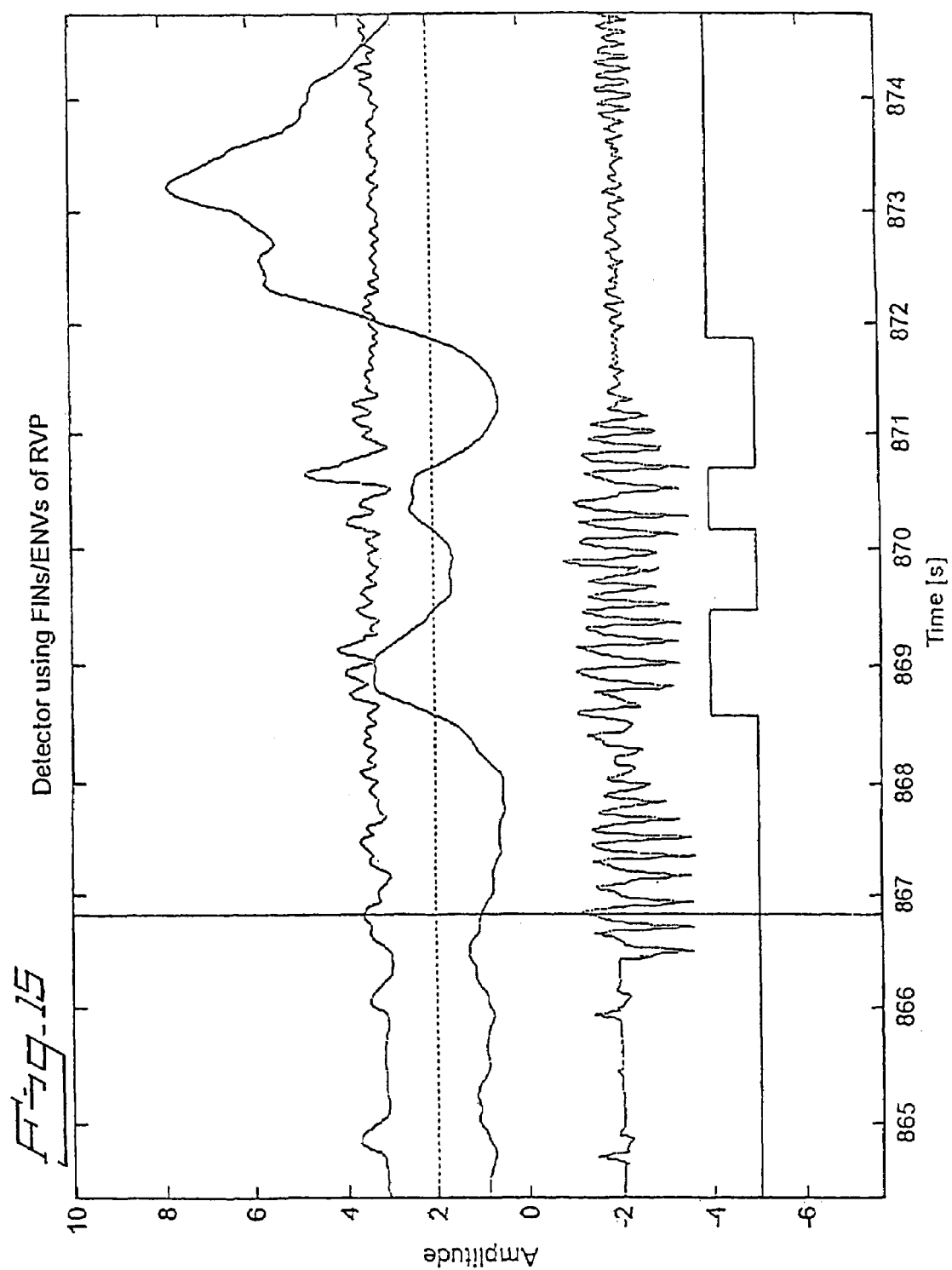
FIG. 15 shows the last part of the legend in FIG. 14 in a greater scale that especially illustrates the onset of the final VF.

FIG. 15 shows the last part of the legend in FIG. 14 in a greater scale that especially illustrates the onset of the final VF.

In a second preferred embodiment the instantaneous amplitude and the instantaneous frequency are used to identify heart conditions.

Figure 16:
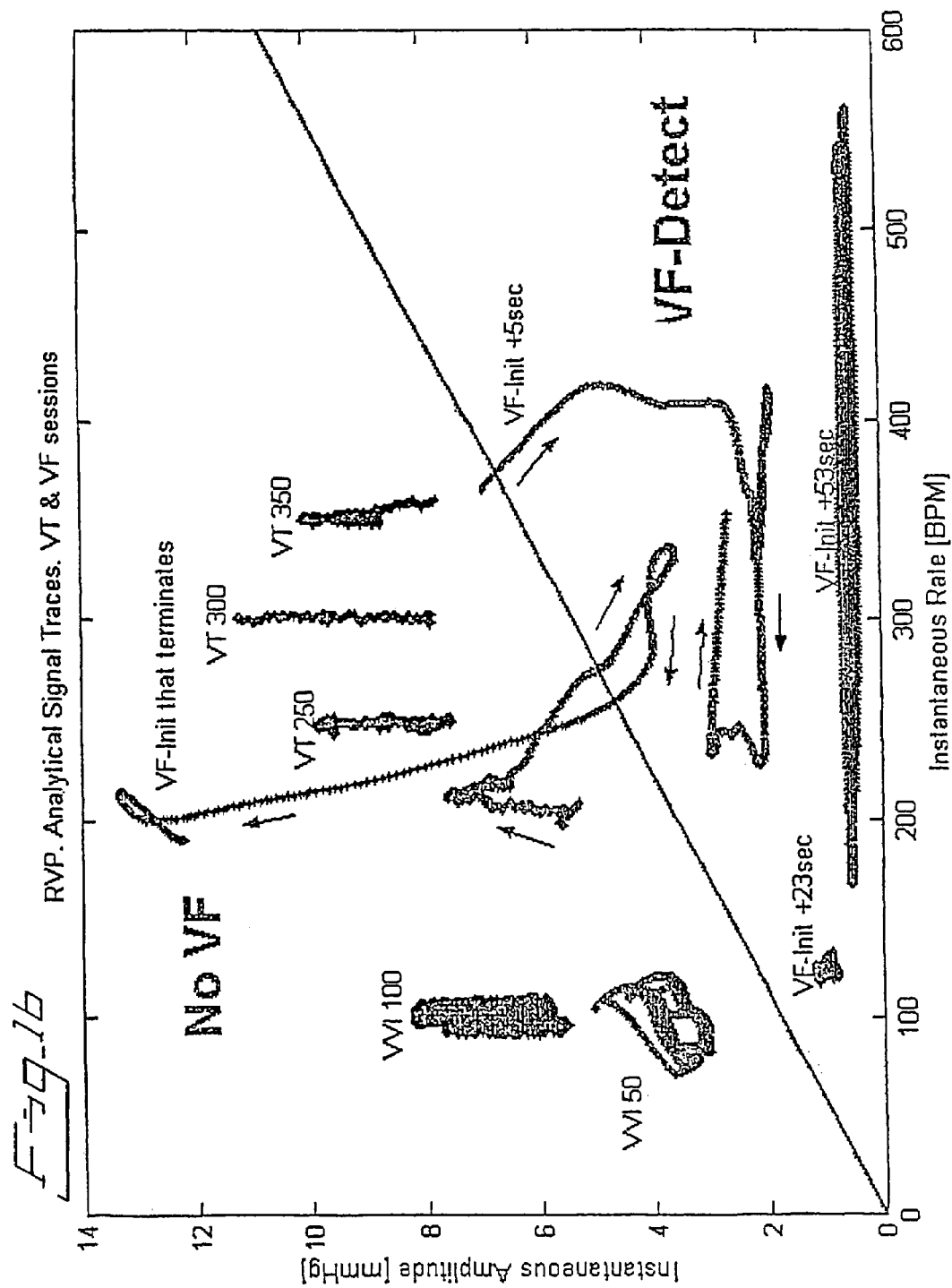
FIG. 16 shows a graphical illustration of this second embodiment of the present invention.

FIG. 16 shows a graphical illustration of this second embodiment having as Y-axis the amplitude in mmHg and as X-axis the frequency in beats per minute (BPM). In this second embodiment the RVP is measured but as will become evident from the further description of the present invention the principle of this second embodiment using both the amplitude and the frequency of the analytic signal is applicable for other heart related parameters as well. A straight line separates the area into a "no VF area" and a "VF-detection area". Short time segments (a few seconds) selected from different situations are shown, where each specific situation is related to a specific area of the plot. In this example the line is the detection threshold at 400% of the normalized value. Ventricular fibrillation is detected when the signals are inside the VF-detection area. A number of different heart conditions or heart stimulator states are indicated in the figure. For example, in the No VF area VVI 50 and VVI 100 heart stimulator states are shown and also three different ventricular tachycardia conditions (VT250, VT300 and VT350). An initiated ventricular fibrillation session that terminates may also be followed. In the VF-detection area some VF conditions are shown at different times after initiation.

In a third preferred embodiment the bipolar right ventricular (RV) intracardiac electrogram (IEGM) was used as heart related parameter.

The signal was pre-processed by a bandpass filter of 0.3-100 Hz and the analytical signal was calculated using a Fast Fourier Transform (FFT).

Figure 17:
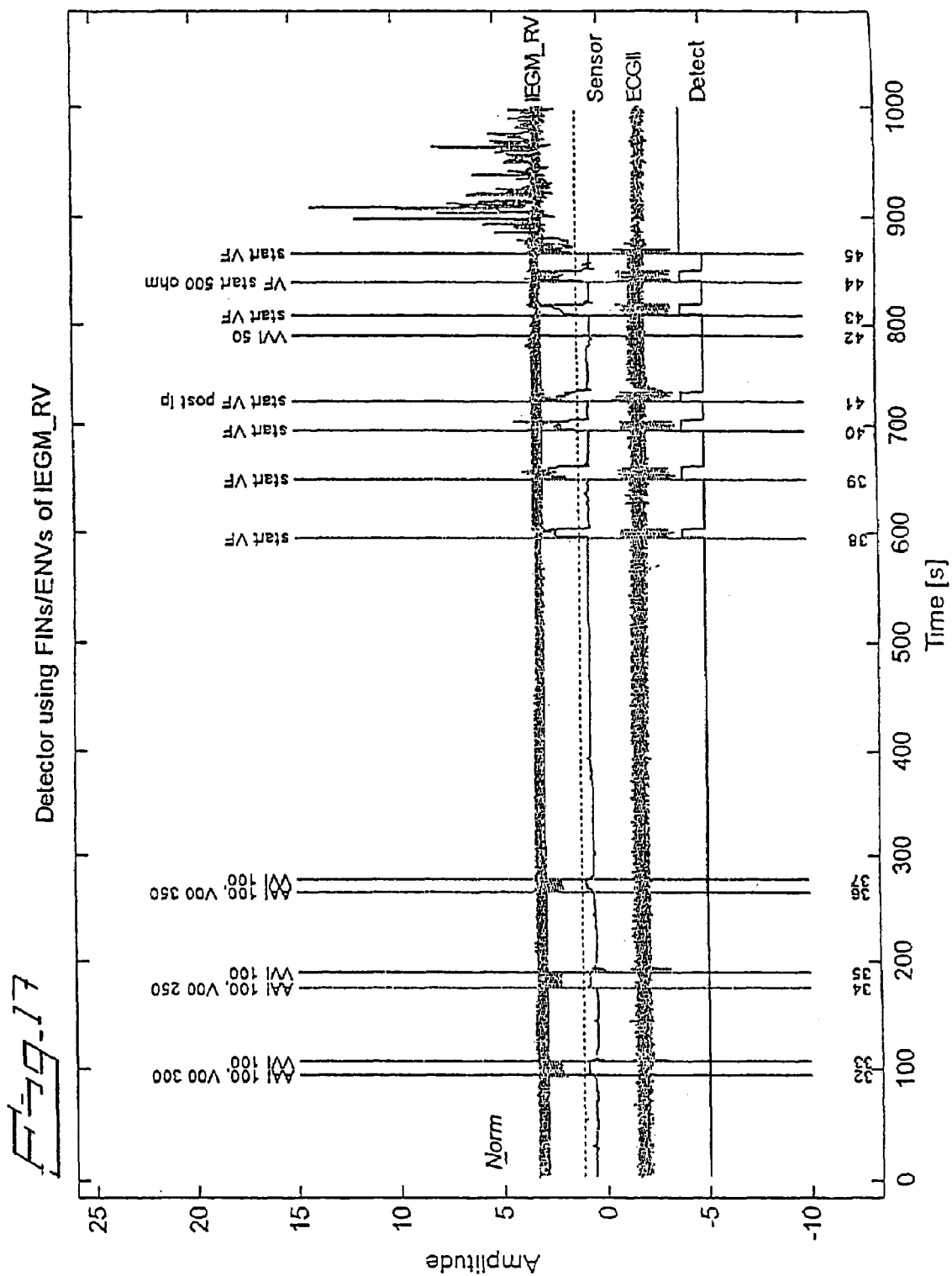
FIG. 17 shows a legend of a ventricular tachycardia (VT) session followed by a ventricular fibrillation (VF) session illustrating an embodiment of the present invention.

In FIG. 17 the processing is performed in a similar way as in the first embodiment by determining the quotient Q=F/E. A normalized value of the quotient Q was used, $Q_{detect}=Q/Q_n$, where $Q_n$, is a 10 seconds average of Q during normal conditions.

FIG. 17 shows a legend of a ventricular tachycardia (VT) session followed by a ventricular fibrillation (VF) session and shows from above the IEGM-RV, a VF detection threshold, $Q_{detect}$, surface ECG and the logical VF-detection signal. The Y-axis represents the amplitude of $Q_{detect}$ and the x-axis the time in seconds.

Figure 18:
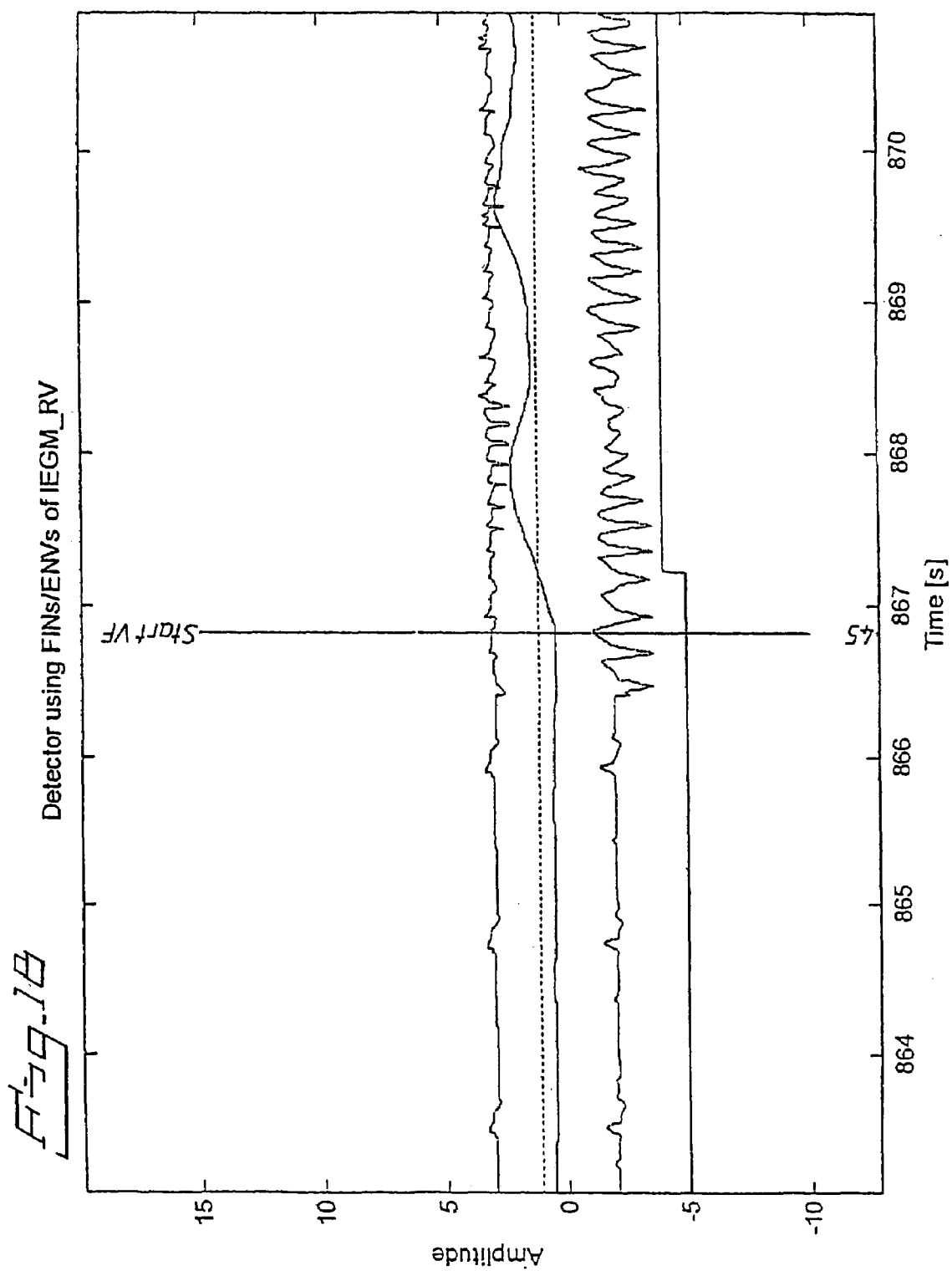
FIG. 18 shows the last part of the legend in FIG. 16 in a greater scale that especially illustrates the onset of the final VF.

FIG. 18 shows the last part of the legend in FIG. 17 in a greater scale that especially illustrates the onset of the final VF.

Figure 19:
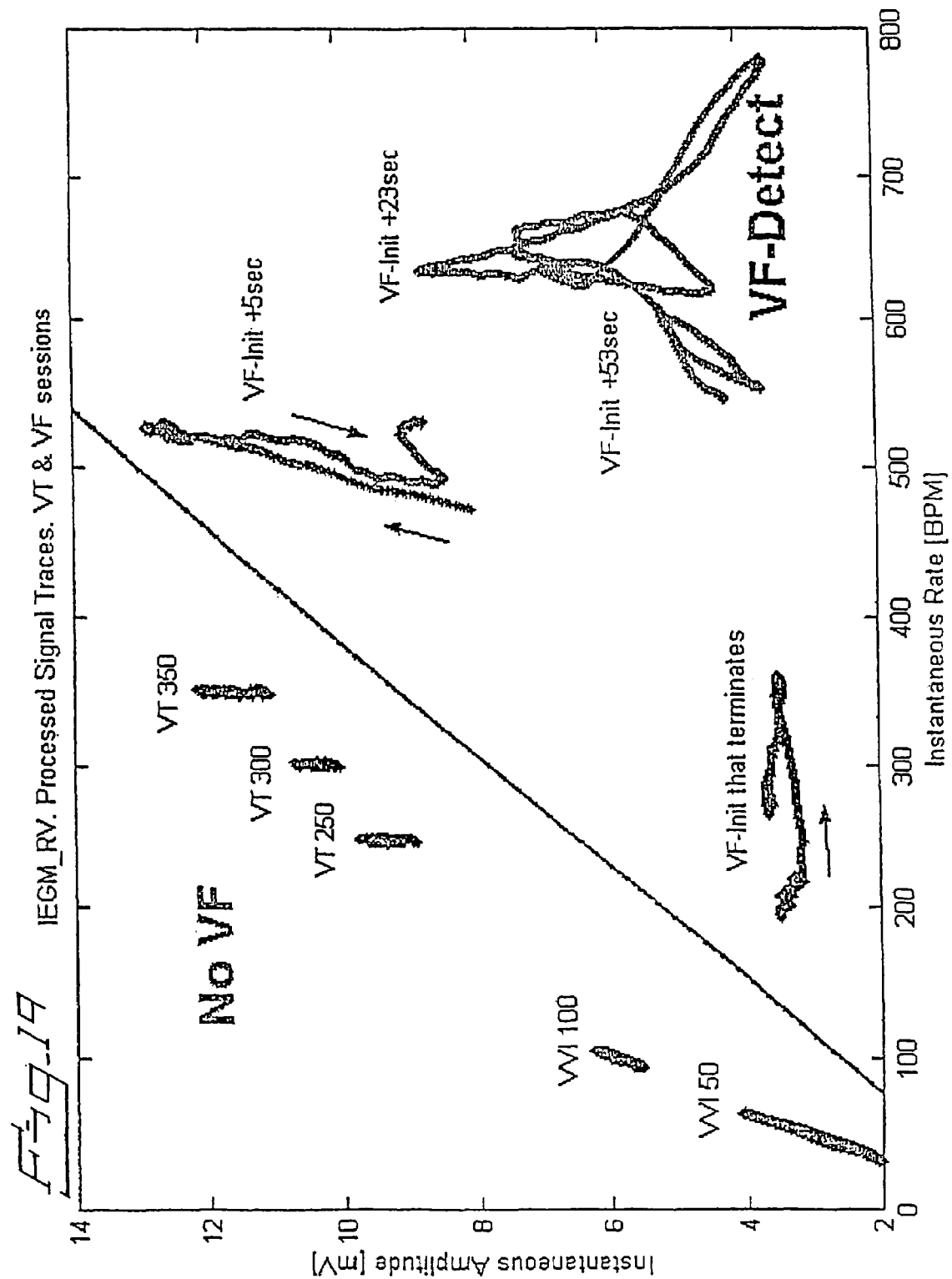
FIG. 19 shows a graphical illustration of the third embodiment of the present invention.

FIG. 19 shows a graphical illustration of this third embodiment having as y-axis the amplitude in mV and as x-axis the frequency in beats per minute (BPM). A straight line separates the area into a "no VF area" and a "VF-detection area". Short time segments (a few seconds) selected from different situations are shown, where each specific situation is related to a specific area of the plot. In this example the line is the 225% threshold. Ventricular fibrillation is detected when the signals are inside the VF-detection area.

Figure 20:
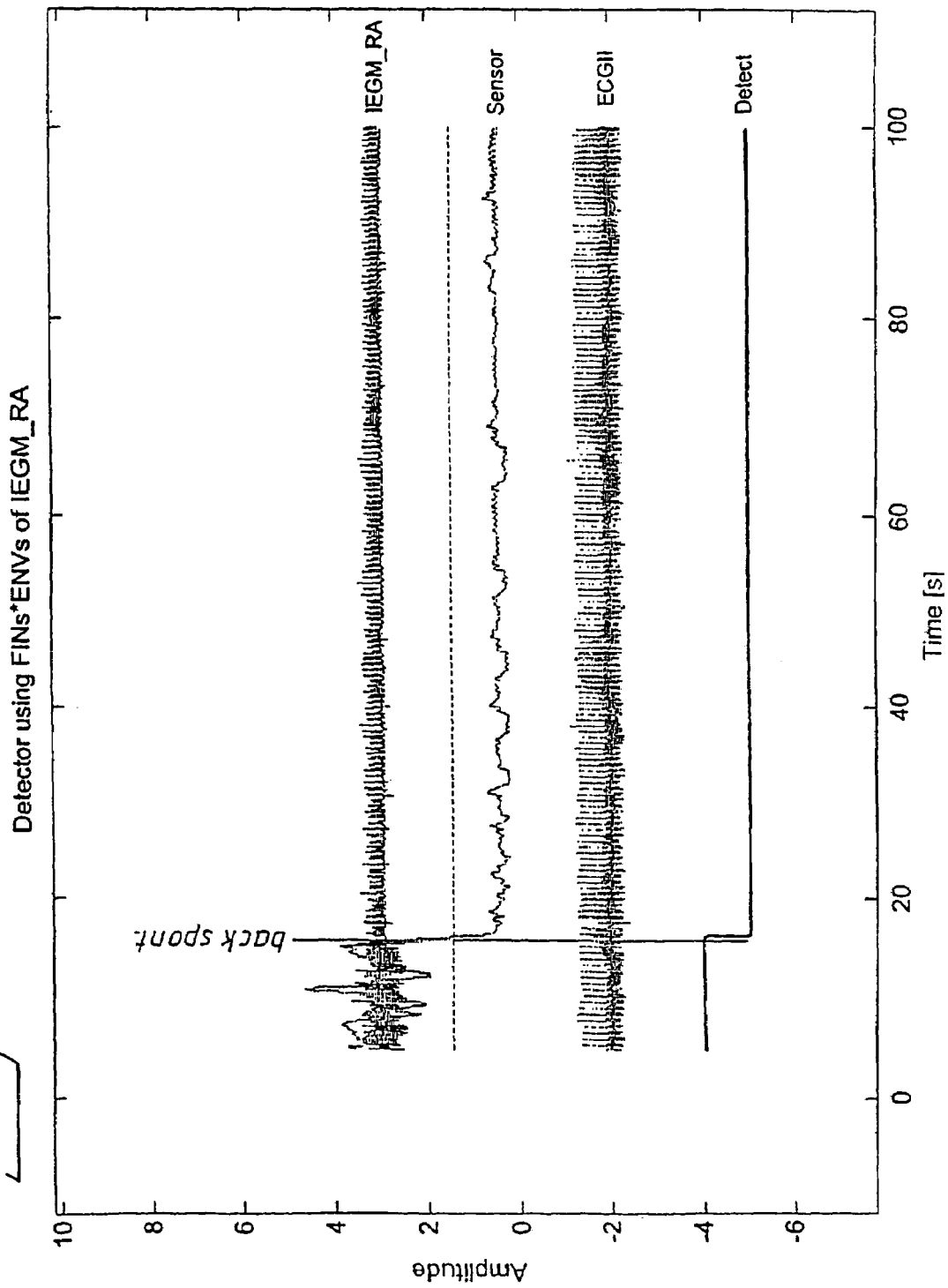
FIG. 20 is an illustration of a fourth embodiment of the present invention where the measured signal is the intracardiac IEGM signal.

FIG. 20 is an illustration of a fourth embodiment of the present invention. The measured signal is the intracardiac IEGM signal measured between tip and ring of an electrode located in the right atrium. The applied processing is the product P=F*E. The sensor signal is a normalized value of the product, Pdetect=P/Pn, where Pn is a 10 seconds average of P during normal conditions. It is an advantage in this case to enhance the detection using the rate and amplitude increase in the IEGM during atrial fibrillation. The figure shows the spontaneous termination of atrial fibrillation and the change to normal sinus rhythm. The detection level was set to 300% in this case.

Figure 21:
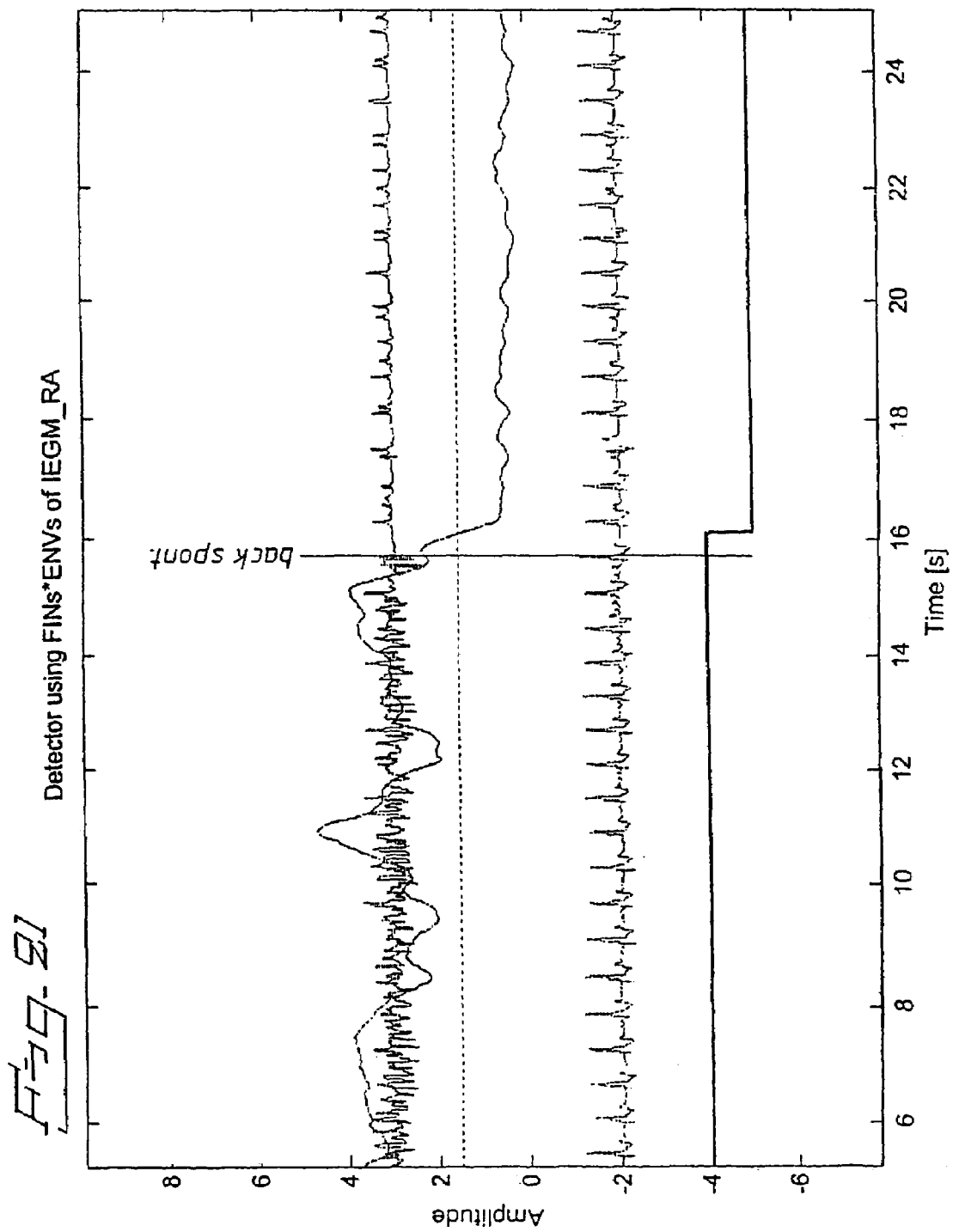
FIG. 21 shows the last part of the legend in FIG. 20 in a greater scale.

FIG. 21 illustrates the fourth embodiment in a greater scale that shows the transition from atrial fibrillation (AF) to sinus rhythm (SR).

Figure 22:
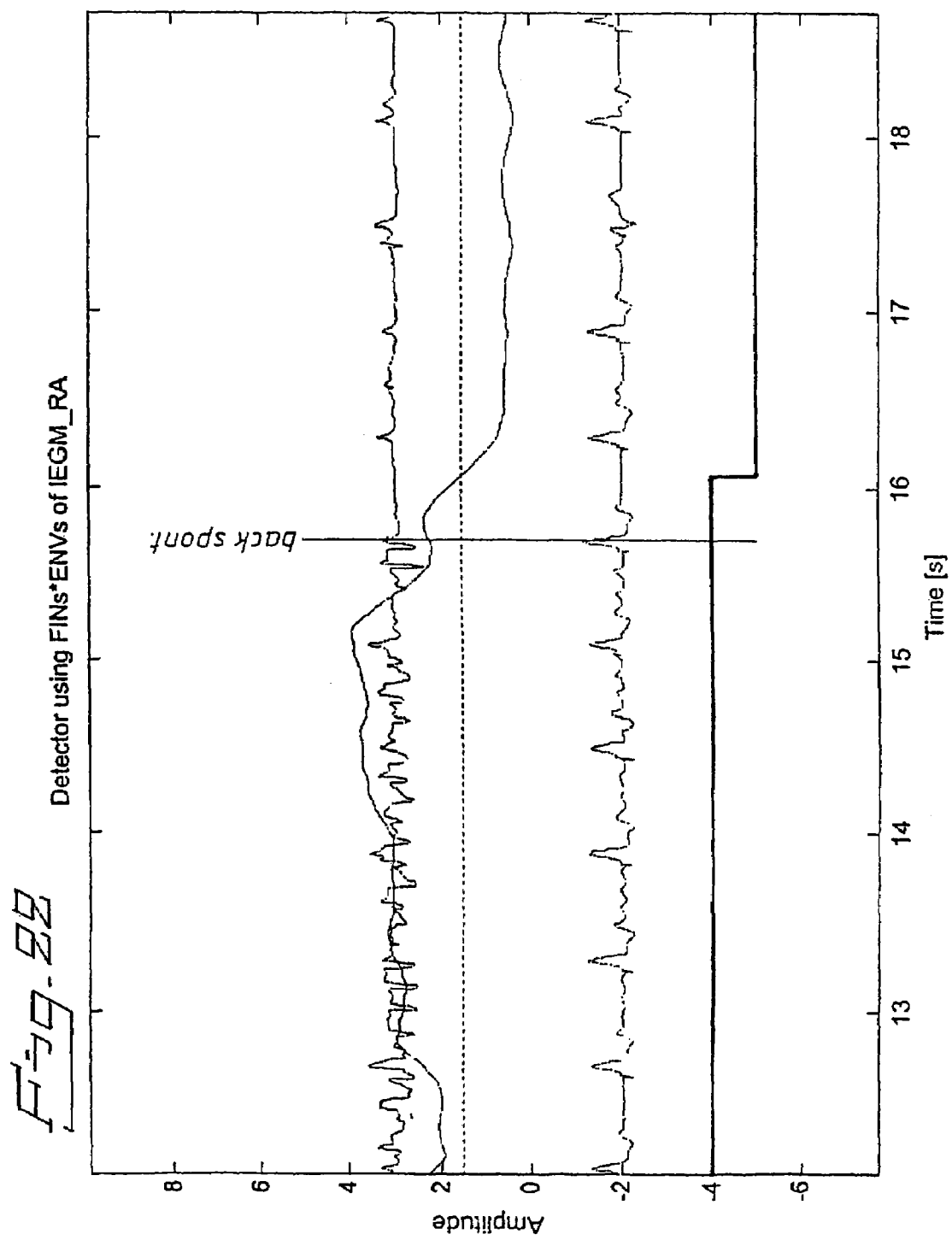
FIG. 22 shows the last part of the legend in FIG. 20 in still a greater scale.

FIG. 22 also illustrates the fourth embodiment in a still greater scale that shows the transition from AF to SR.

Figure 23:
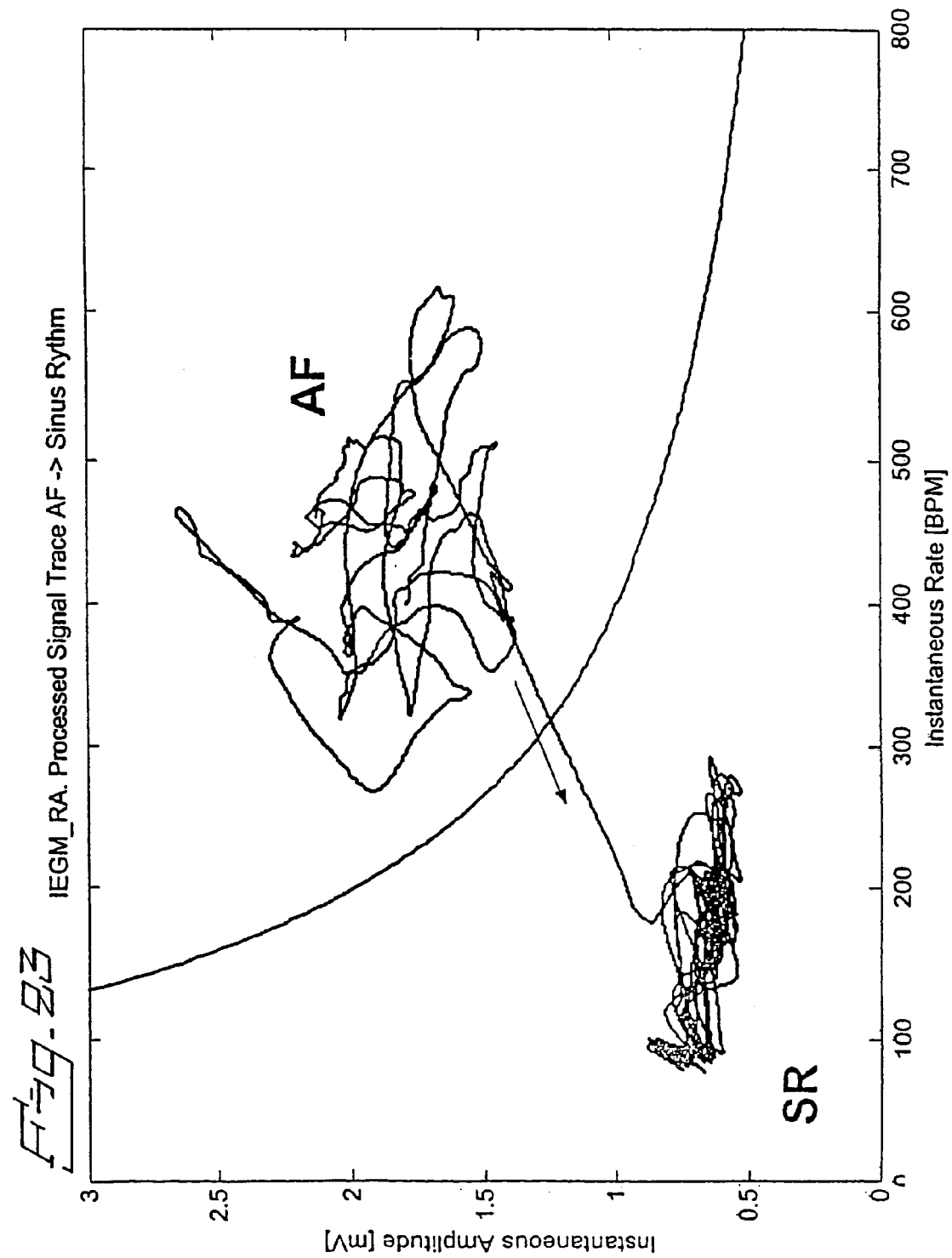
FIG. 23 is a graphical illustration of the fourth embodiment.

FIG. 23 is a graphical illustration of the fourth embodiment. The whole data segment in the plot illustrated in FIG. 20 is shown: The axes are the calculated rate and amplitude, respectively, obtained from the analytical signal. The threshold, in this case a hyperbola, separates the area into a "Sinus Rhythm area" (SR) and an "Atrial Fibrillation area" (AF). The arrow marks the transition between the two states, which is detected within a second.

Figure 24:
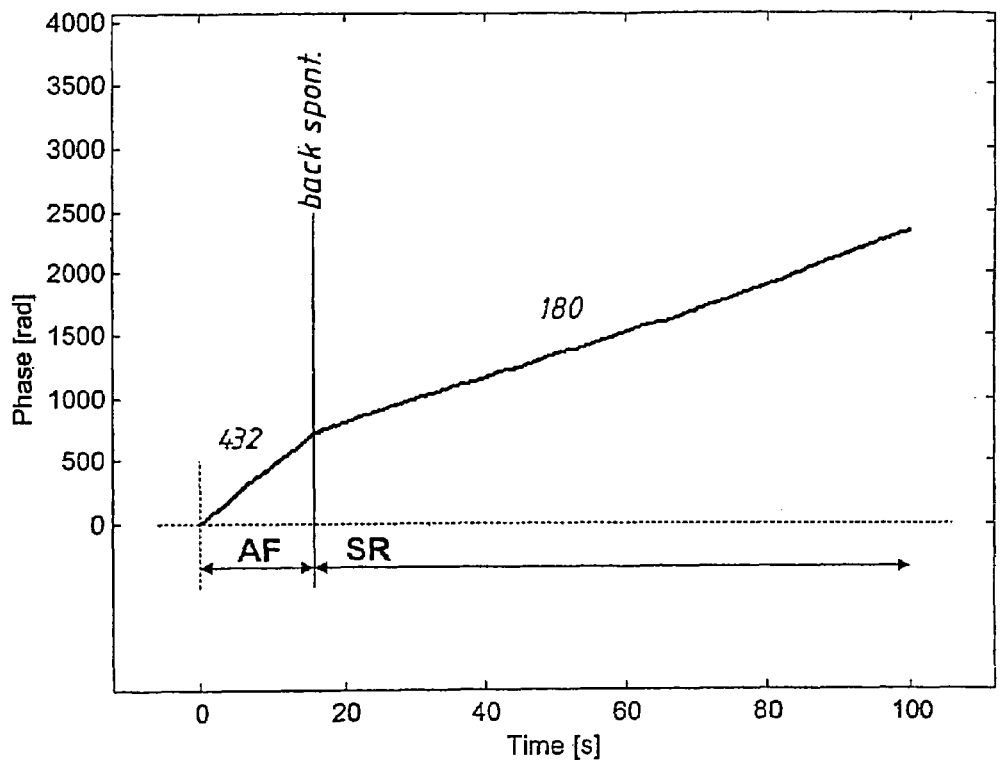
FIG. 24 shows a graphical illustration of the calculated phase of the IEGM.

The calculated phase information φ(t) is not used in these embodiments other than as a source for the calculated frequency. The instantaneous frequency is the slope of the phase φ(t). FIG. 24 shows the calculated phase of the IEGM. The two italic numbers is the average slope in BPM within the AF and SR intervals calculated by linear regression. A possible application for the phase could be to evaluate phase locking of the IEGM-signal the other measured parameters in the heart for diagnostic purposes.

Figure 25:
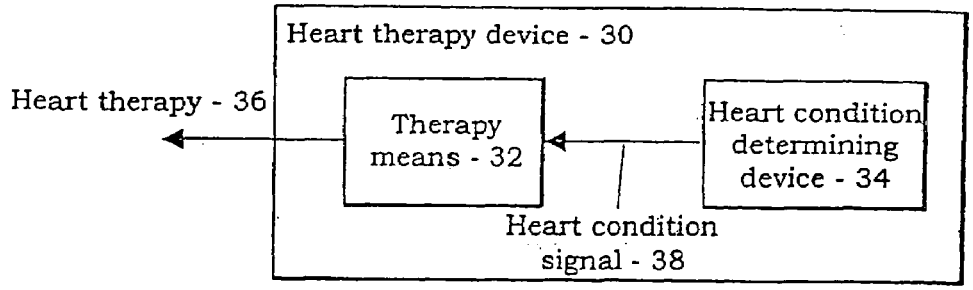
FIG. 25 shows a block diagram illustrating an implantable heart therapy device according to the present invention.

The present invention also relates to an implantable heart therapy device, which is illustrated in the block diagram shown in FIG. 25. The heart therapy device 30 includes a therapy unit 32 and the heart condition determining device 34 as described above. The therapy unit 32 is adapted to initiate an adequate heart therapy 36 in dependence of the heart condition signal 38. Those skilled in the art of heart therapy are aware of numerous different therapy devices, e.g. implantable heart stimulators and implantable heart defibrillators/cardioverters.

According to a still further embodiment of the present invention the heart therapy device also includes a confirmation unit that confirms a "new" heart condition that occurs after a specific therapy successfully has been applied to the heart. These confirmation units may include detectors for detecting IEGM and/or the heart rate.

Although modifications and changes may be suggested by those skilled in the art, it is the invention of the inventor to embody within the patent warranted heron all changes and modifications as reasonably and properly come within the scope of his contribution to the art.

The invention claimed is:

1. An implantable device for determining a cardiac condition comprising:
    a detector adapted to substantially continuously detect a heart-related signal not limited by a cardiac cycle and for forming an input signal therefrom;
    an analysis unit connected to said detector and receiving said input signal therefrom, and producing a continuous analysis signal from said input signal having a real part substantially corresponding to said input signal and an imaginary part formed as a predetermined transformation of said input signal;
    a calculation unit connected to said analysis unit and receiving said analysis signal therefrom, said calculation unit calculating at least two heart-related parameters from said analysis signal dependent on said real part and said imaginary part; and
    a processing unit connected to said calculation unit and supplied with said heart-related parameters therefrom, said processing unit combining said heart-related parameters in a predetermined manner and identifying a cardiac condition therefrom.

2. A device as claimed in claim 1 wherein said analysis unit transforms said input signal uses the Hilbert transform to form said imaginary part of said analysis signal.

3. A device as claimed in claim 1 wherein said analysis unit transforms said input signal using an approximate Hilbert transform to form said imaginary part of said analysis signal.

4. A device as claimed in claim 1 wherein said detector is adapted to obtain a signal indicative of right ventricular pressure as said heart-related signal.

5. A device as claimed in claim 1 wherein said detector is adapted to detect an intracardiac electrogram from the right ventricle as said heart-related signal.

6. A device as claimed in claim 1 wherein said calculation unit calculates three heart-related parameters, consisting of an instantaneous amplitude, a frequency and a phase of said analysis signal.

7. A device as claimed in claim 1 wherein said processing unit combines said heart-related parameters by forming a quotient of two of said heart-related parameters.

8. A device as claimed in claim 7 wherein said calculation unit determines a frequency and an amplitude of said analysis signal as said at least two heart-related parameters, and wherein said processing unit forms said quotient between said frequency and said amplitude.

9. A device as claimed in claim 1 wherein said processing unit combines said at least two heart-related parameters by forming a product of at least two of said at least two heart-related parameters.

10. A device as claimed in claim 9 wherein said calculation unit determines a frequency and an amplitude of said analysis signal as said at least two heart-related parameters, and wherein said processing unit forms said product between said frequency and said amplitude.

11. A device as claimed in claim 1 wherein said processing unit combines said at least two heart-related parameters by plotting two of said at least two heart-related parameters in a diagram having a threshold line dividing said diagram into respective detection areas.

12. A device as claimed in claim 11 wherein said calculating unit calculates an amplitude and a frequency as said two of said at least two heart-related parameters, and wherein said processing unit plots said amplitude and said frequency along respective axes of said diagram.

13. A device as claimed in claim 1 wherein said analysis unit comprises at least one finite impulse response filter acting on said input signal.

14. A device as claimed in claim 1 wherein said analysis unit comprises at least one infinite impulse response filter acting on said input signal.

15. A device as claimed in claim 1 wherein said calculation unit calculates an absolute value, representing an instantaneous amplitude, of said analysis signal as one of said at least two heart-related parameters.

16. A device as claimed in claim 1 wherein said calculation unit calculates an instantaneous frequency of said analysis signal as one of said at least two heart-related parameters.

17. A device as claimed in claim 11 wherein said processing unit detects a fibrillation, selected from the group consisting of atrial fibrillation and ventricular fibrillation, from said combination of heart-related parameters, as said cardiac condition.

18. An implantable cardiac therapy device comprising:
a cardiac condition determining device comprising a detector adapted to substantially continuously detect a heart-related signal not limited by a cardiac cycle and forming an input signal therefrom, an analysis unit connected to said detector and receiving said input signal therefrom, and producing a continuous analysis signal from said input signal having a real part substantially corresponding to said input signal and an imaginary part formed as a predetermined transformation of said input signal, a calculation unit connected to said analysis unit and receiving said analysis signal therefrom, said calculation unit calculating at least two heart-related parameters from said analysis signal dependent on said real part and said imaginary part, and a processing unit connected to said calculation unit and supplied with said heart-related parameters therefrom, said processing unit combining said heart-related parameters in a predetermined manner and identifying a cardiac condition therefrom; and
a therapy administering unit connected to said cardiac condition determining device and adapted to deliver a selected cardiac therapy dependent on said cardiac condition.

19. A method for determining a cardiac condition comprising the steps of:
substantially continuously detecting a heart-related signal in vivo and for forming an input signal therefrom;
electronically producing a continuous analysis signal from said input signal having a real part substantially corresponding to said input signal and an imaginary part formed as a predetermined transformation of said input signal;
electronically calculating at least two heart-related parameters from said analysis signal dependent on said real part and said imaginary part; and
electronically combining said heart-related parameters in a predetermined manner for identifying a cardiac condition.

20. A method as claimed in claim 19 comprising transforming said input signal using the Hilbert transform to form said imaginary part of said analysis signal.

21. A method as claimed in claim 19 comprising transforming said input signal using an approximate Hilbert transform to form said imaginary part of said analysis signal.

22. A method as claimed in claim 19 comprising obtaining a signal indicative of right ventricular pressure as said heart-related signal.

23. A method as claimed in claim 19 comprising detecting an intracardiac electrogram from the right ventricle as said heart-related signal.

24. A method as claimed in claim 19 comprising electronically calculating three heart-related parameters, consisting of an instantaneous amplitude, a frequency and a phase of said analysis signal as said at least two heart-related parameters.

25. A method as claimed in claim 19 comprising electronically combining said heart-related parameters by forming a quotient of two of said heart-related parameters.

26. A method as claimed in claim 25 comprising electronically determining a frequency and an amplitude of said analysis signal as said at least two heart-related parameters, and forming said quotient between said frequency and said amplitude.

27. A method as claimed in claim 19 comprising electronically combining said at least two heart-related parameters by forming a product of at least two of said at least two heart-related parameters.

28. A method as claimed in claim 27 comprising electronically determining a frequency and an amplitude of said analysis signal as said at least two heart-related parameters, and forming said product between said frequency and said amplitude.

29. A method as claimed in claim 19 comprising electronically combining said at least two heart-related parameters by plotting two of said at least two heart-related parameters in an electronic diagram having a threshold line dividing said electronic diagram into respective detection areas.

30. A method as claimed in claim 29 comprising electronically calculating an amplitude and a frequency as said two of said at least two heart-related parameters, and plotting said amplitude and said frequency along respective axes of said electronic diagram.

31. An implantable device for determining a cardiac condition comprising:
a detector adapted to detect a right ventricular pressure signal from a heart and for forming an input signal therefrom;
an analysis unit connected to said detector and receiving said input signal therefrom, and producing an analysis signal from said input signal having a real part substantially corresponding to said input signal and an imaginary part formed as an at least approximate Hilbert transformation of said input signal;

a calculation unit connected to said analysis unit and receiving said analysis signal therefrom, said calculation unit calculating at least two heart-related parameters from said analysis signal dependent on said real part and said imaginary part; and a processing unit connected to said calculation unit and supplied with said heart-related parameters therefrom, said processing unit combining said heart-related parameters in a predetermined manner and identifying a cardiac condition of the heart therefrom selected from the group consisting of actual fibrillation and ventricular fibrillation.

32. An implantable cardiac therapy device comprising:

a cardiac condition determining device comprising a detector adapted to detect a right ventricular pressure signal from a heart and and forming an input signal therefrom, an analysis unit connected to said detector and receiving said input signal therefrom, and producing an analysis signal from said input signal having a real part substantially corresponding to said input signal and an imaginary part formed as an at least approximate Hilbert—transformation of said input signal, a calculation unit connected to said analysis unit and receiving said analysis signal therefrom, said calculation unit calculating at least two heart-related parameters from said analysis signal dependent on said real part and said imaginary part, and a processing unit connected to said calculation unit and supplied with said heart-related parameters therefrom, said processing unit combining said heart-related parameters in a predetermined manner and identifying a cardiac condition of the heart therefrom selected from the group consisting of atrial fibrillation and ventricular fibrillation; and a therapy administering unit connected to said cardiac condition determining device and adapted to deliver a selected cardiac therapy dependent on said defibrillation condition.

33. A method for determining a cardiac condition comprising the steps of:

detecting a right ventricular pressure signal in vivo and for forming an input signal therefrom;

electronically producing an analysis signal from said input signal having a real part substantially corresponding to said input signal and an imaginary part formed as an at least approximate Hilbert transformation of said input signal;

electronically calculating at least two heart-related parameters from said analysis signal dependent on said real part and said imaginary part; and electronically combining said heart-related parameters in a predetermined manner and identifying a cardiac condition of the heart therefrom selected from the group consisting of atrial fibrillation and ventricular fibrillation.

* * * * *